(12) United States Patent
Elrod

(10) Patent No.: US 8,257,648 B2
(45) Date of Patent: Sep. 4, 2012

(54) SYSTEM AND METHOD FOR REDUCING ODORS IN A BLIND

(76) Inventor: Scott Elrod, Angleton, TX (US)

(*) Notice: Subject to any disclaimer, the term of this patent is extended or adjusted under 35 U.S.C. 154(b) by 0 days.

(21) Appl. No.: 13/302,886

(22) Filed: Nov. 22, 2011

(65) Prior Publication Data

US 2012/0063951 A1  Mar. 15, 2012

Related U.S. Application Data

(60) Continuation-in-part of application No. 12/660,347, filed on Feb. 24, 2010, now Pat. No. 8,066,939, which is a division of application No. 11/714,083, filed on Mar. 5, 2007, now abandoned, which is a continuation-in-part of application No. 11/018,620, filed on Dec. 21, 2004, now Pat. No. 7,939,015, and a continuation-in-part of application No. 12/800,721, filed on May 21, 2010, which is a continuation-in-part of application No. 12/456,944, filed on Jun. 24, 2009, which is a continuation-in-part of application No. 12/326,240, filed on Dec. 2, 2008, which is a continuation-in-part of application No. 11/714,083, filed on Mar. 5, 2007, now abandoned, which is a continuation-in-part of application No. 11/018,620, filed on Dec. 21, 2004, now Pat. No. 7,939,015.

(51) Int. Cl.
*A61L 9/00* (2006.01)

(52) U.S. Cl. ............... 422/5; 422/28; 422/29; 422/120; 422/123

(58) Field of Classification Search .................. 422/4, 5, 422/28, 29, 120, 123
See application file for complete search history.

(56) References Cited

U.S. PATENT DOCUMENTS

| | | | |
|---|---|---|---|
| 1,961,878 A | 6/1934 | Gilkey | |
| 2,203,188 A | 6/1940 | Beer | |
| 3,214,364 A | 10/1965 | Van Tuyle et al. | |
| 3,421,836 A | 1/1969 | Sundin et al. | |

(Continued)

FOREIGN PATENT DOCUMENTS

EP  0261987  3/1988

(Continued)

OTHER PUBLICATIONS

Amazon.com: Sensidyne Gas Detection Tubes, Ozone: Industrial & Scientific. Jul. 19, 2011. <http://www.amazon.com/s/ref=nb_sb_noss/185-2249298-3532721?url=search-alias%3Daps&field-keywords=Sensidyne+Gas+Detection+Tubes>.

(Continued)

*Primary Examiner* — Sean E Conley
(74) *Attorney, Agent, or Firm* — Morriss O'Bryant Compagni, PC

(57) ABSTRACT

The present invention provides a method and apparatus for controlling a concentration of descenting particles within a temporary structure. The temporary structure comprises a plurality of sidewalls and a roof interconnecting the sidewalls. A plurality of selectively openable and closeable upper windows and lower vents are disposed in the sidewalls. The lower vents are disposed at a location below the upper windows. An ozone generator is disposed within and coupled to the temporary structure to produce descenting particles that are controlled within a hunting zone of the temporary structure to be between about 0.04 and 0.1 ppm.

18 Claims, 17 Drawing Sheets

U.S. PATENT DOCUMENTS

| | | | |
|---|---|---|---|
| 3,601,292 A | 8/1971 | Bliss | |
| 3,670,425 A | 6/1972 | Benjamin | |
| 3,750,556 A | 8/1973 | Duke et al. | |
| 3,937,967 A | 2/1976 | Steinitz | |
| 3,949,056 A | 4/1976 | Nakshbendi | |
| 4,045,316 A | 8/1977 | Legan | |
| 4,238,857 A | 12/1980 | Waters | |
| 4,309,388 A | 1/1982 | Tenney et al. | |
| 4,374,571 A | 2/1983 | Hirvela | |
| 4,735,010 A | 4/1988 | Grinarml | |
| 4,811,159 A | 3/1989 | Foster, Jr. | |
| 4,838,293 A | 6/1989 | Novak | |
| 4,863,687 A | 9/1989 | Stevens et al. | |
| 4,867,052 A | 9/1989 | Cipelletti | |
| 4,904,289 A | 2/1990 | Miyakami et al. | |
| 4,941,270 A | 7/1990 | Hoffman | |
| 4,953,674 A | 9/1990 | Landes | |
| 4,990,311 A | 2/1991 | Hiari et al. | |
| 5,087,426 A | 2/1992 | Inoue et al. | |
| 5,152,077 A | 10/1992 | Liang | |
| 5,185,129 A | 2/1993 | Koutrakis et al. | |
| 5,192,500 A | 3/1993 | Treddenick | |
| 5,195,922 A | 3/1993 | Genco | |
| 5,303,496 A | 4/1994 | Kowalkowski | |
| 5,316,182 A | 5/1994 | Lee et al. | |
| 5,342,415 A | 8/1994 | Wasinger et al. | |
| 5,383,236 A | 1/1995 | Sesselmann | |
| 5,429,271 A | 7/1995 | Porter | |
| 5,433,230 A | 7/1995 | Miller | |
| 5,433,919 A | 7/1995 | Baltes | |
| 5,457,054 A | 10/1995 | Geisinger et al. | |
| 5,468,454 A | 11/1995 | Kim | |
| 5,484,472 A | 1/1996 | Weinberg | |
| 5,514,345 A | 5/1996 | Garbutt et al. | |
| 5,520,893 A | 5/1996 | Kasting, Jr. et al. | |
| 5,539,930 A | 7/1996 | Sesselmann | |
| 5,547,476 A | 8/1996 | Siklosi | |
| 5,626,820 A | 5/1997 | Kinkead et al. | |
| 5,664,995 A | 9/1997 | O'Keefe | |
| 5,667,564 A | 9/1997 | Weinberg | |
| 5,681,355 A | 10/1997 | Davis et al. | |
| 5,704,833 A | 1/1998 | Reix et al. | |
| 5,762,648 A | 6/1998 | Yeazell | |
| 5,765,584 A | 6/1998 | Heisler et al. | |
| 5,766,560 A | 6/1998 | Cole | |
| 5,789,368 A | 8/1998 | You et al. | |
| 5,790,987 A | 8/1998 | Sesselmann | |
| 5,795,544 A | 8/1998 | Matz | |
| 5,829,066 A | 11/1998 | Aibe | |
| 5,833,740 A | 11/1998 | Brais | |
| 5,835,840 A | 11/1998 | Goswami | |
| 5,891,391 A | 4/1999 | Fore | |
| 5,911,957 A | 6/1999 | Khatchatrian | |
| 5,931,014 A | 8/1999 | Cole | |
| 5,941,264 A | 8/1999 | Gregg | |
| 5,942,438 A | 8/1999 | Antonoplos et al. | |
| 5,983,834 A | 11/1999 | Tai | |
| 6,007,770 A | 12/1999 | Peiper et al. | |
| 6,009,559 A | 1/2000 | Sesselmann | |
| 6,074,608 A | 6/2000 | Matz | |
| 6,094,549 A | 7/2000 | Hiraoka | |
| 6,134,718 A | 10/2000 | Sesselmann | |
| 6,134,806 A | 10/2000 | Dhaemers | |
| 6,149,038 A | 11/2000 | Tsai | |
| 6,153,111 A | 11/2000 | Conrad et al. | |
| 6,156,268 A | 12/2000 | Curry et al. | |
| 6,163,098 A | 12/2000 | Taylor et al. | |
| 6,182,671 B1 | 2/2001 | Taylor et al. | |
| 6,218,189 B1 | 4/2001 | Antonoplos et al. | |
| 6,267,242 B1 | 7/2001 | Nagata et al. | |
| 6,284,204 B1 | 9/2001 | Cole et al. | |
| 6,312,507 B1 | 11/2001 | Taylor et al. | |
| 6,336,964 B1 | 1/2002 | Omatsu et al. | |
| 6,340,447 B2 | 1/2002 | Johnson | |
| 6,340,497 B2 | 1/2002 | Wilson | |
| 6,355,216 B1 | 3/2002 | Kristiansson et al. | |
| 6,368,867 B1 | 4/2002 | Gibson et al. | |
| 6,379,435 B1 | 4/2002 | Fukunaga et al. | |
| 6,503,547 B1 | 1/2003 | Lima | |
| 6,564,591 B2 | 5/2003 | Noyes et al. | |
| 6,565,805 B2 | 5/2003 | Khatchatrian et al. | |
| 6,576,190 B1 | 6/2003 | Park | |
| RE38,231 E * | 8/2003 | Fargason | 135/93 |
| 6,613,277 B1 | 9/2003 | Monagan | |
| 6,630,105 B1 | 10/2003 | O'Neill et al. | |
| 6,632,407 B1 | 10/2003 | Lau et al. | |
| 6,635,439 B2 | 10/2003 | Morrison et al. | |
| D486,357 S | 2/2004 | Leba et al. | |
| 6,790,411 B1 | 9/2004 | Read | |
| 6,896,853 B2 | 5/2005 | Lau et al. | |
| 6,941,961 B1 | 9/2005 | Eastman, II | |
| 6,967,008 B1 | 11/2005 | Barnes | |
| 7,040,335 B1 * | 5/2006 | Ransom | 135/117 |
| 7,117,687 B2 | 10/2006 | Naaman | |
| 7,118,608 B2 | 10/2006 | Lovell | |
| 7,121,290 B2 | 10/2006 | Eastman, II | |
| 7,128,077 B2 | 10/2006 | Cantwell | |
| 7,186,373 B2 | 3/2007 | Centanni | |
| 7,222,634 B2 * | 5/2007 | Hess et al. | 135/93 |
| 7,325,364 B2 | 2/2008 | Leininger et al. | |
| 7,475,699 B2 | 1/2009 | Johnson et al. | |
| 7,493,910 B1 | 2/2009 | Ransom | |
| 7,565,909 B2 | 7/2009 | Reis et al. | |
| 7,662,636 B2 | 2/2010 | Maruo et al. | |
| D621,898 S | 8/2010 | Smith | |
| 7,939,015 B1 | 5/2011 | Elrod | |
| 2002/0030022 A1 | 3/2002 | Bradley | |
| 2002/0069904 A1 | 6/2002 | Robinson | |
| 2002/0071795 A1 | 6/2002 | Jensen | |
| 2002/0094298 A1 | 7/2002 | Monagan | |
| 2003/0044308 A1 | 3/2003 | Toth | |
| 2003/0066767 A1 | 4/2003 | Felsenthal | |
| 2003/0089010 A1 | 5/2003 | Wechter et al. | |
| 2003/0108460 A1 | 6/2003 | Andreev et al. | |
| 2003/0111435 A1 | 6/2003 | Chen | |
| 2004/0002349 A1 | 1/2004 | Yamagishi et al. | |
| 2004/0047775 A1 | 3/2004 | Lau et al. | |
| 2004/0096354 A1 | 5/2004 | Nomura et al. | |
| 2004/0149329 A1 | 8/2004 | Hess et al. | |
| 2004/0163184 A1 | 8/2004 | Waldron et al. | |
| 2004/0221396 A1 | 11/2004 | Johnson | |
| 2005/0000555 A1 | 1/2005 | Besse | |
| 2005/0045220 A1 | 3/2005 | Sumner | |
| 2005/0186108 A1 | 8/2005 | Fields | |
| 2005/0207951 A1 | 9/2005 | Lee et al. | |
| 2006/0006122 A1 | 1/2006 | Burns et al. | |
| 2006/0096331 A1 | 5/2006 | Kim | |
| 2006/0151896 A1 | 7/2006 | Wang | |
| 2007/0092414 A1 | 4/2007 | Malyon | |
| 2007/0166186 A1 | 7/2007 | Stec | |
| 2007/0212253 A1 | 9/2007 | Elrod | |
| 2008/0036594 A1 | 2/2008 | Kates | |
| 2009/0038555 A1 | 2/2009 | Reese | |
| 2009/0139459 A1 | 6/2009 | Habacivch et al. | |
| 2009/0301536 A1 | 12/2009 | Cantwell | |
| 2010/0071633 A1 | 3/2010 | Elrod | |
| 2010/0107991 A1 | 5/2010 | Elrod | |
| 2010/0226819 A1 | 9/2010 | Elrod | |
| 2010/0275352 A1 * | 11/2010 | Beeson et al. | 4/144.1 |
| 2010/0289655 A1 | 11/2010 | Elrod et al. | |

FOREIGN PATENT DOCUMENTS

| | | |
|---|---|---|
| JP | 1100948 A | 4/1989 |
| JP | 06-327749 | 11/1994 |
| JP | 09239018 | 9/1997 |
| JP | 09262141 | 10/1997 |
| JP | 11009948 A | 1/1999 |
| JP | 11009949 A | 1/1999 |
| JP | 11226106 A | 8/1999 |
| JP | 11226108 A | 8/1999 |
| JP | 2003001237 A | 1/2003 |
| JP | 2003024426 A | 1/2003 |
| WO | WO 01/51096 | 7/2001 |
| WO | WO 03/089017 | 10/2003 |
| WO | WO 2004067043 | 8/2004 |

| | | |
|---|---|---|
| WO | WO 2005/021135 | 3/2005 |
| WO | WO 2005/056954 | 6/2005 |
| WO | WO 2005/077425 | 8/2005 |

OTHER PUBLICATIONS

Gastec Precision Gas Analysis Apparatus—Air—Environmental Systems—Earth & Environmental. Carolina Biological Supply Company: World-Class Support for Science & Math. Jul. 19, 2011. <http://www.carolina.com/product/gastec+precision+gas+analysis+apparatus.do?keyword=gastec&sortby=bestMatches>.

Ozone Badge—Easy to Use. Ozone Solutions, Inc. Jul. 19, 2011. <http://www.ozonesolutions.com/B1-C.html>.

Ozone Drager Detector Tube, Pkg. of 10, 6746. Lab Safety Supply. Jul. 19, 2011. <http://www.labsafety.com/ozone-drger-detector-tube-pkg-of-10__s__6746/>.

Bomms Terminator. Game Finder—Outdoor Enhancement Systems, Web page print outs from http://www.game-finder.com/bomms-terminator.aspx, printed on Dec. 23, 2006 (2 pages). [cited in PCT/US2005/004322].

Bomms Terminator, Game Finder, May 24, 2002.

Terminator 800, Game Finder, Feb. 13, 2003.

Detection of the cyanobacterial hepatotoxins microcystins; in Toxicology & Applied Pharmacology, McElhiney et al., Dec. 2003 (pp. 219-230).

Fehrenbacher, Jill. Robotic Pollution-Sniffing Eco Dogs! [on-line], Feb. 26, 2007; retrieved from the internet: URL: http://inhabitat.com/robotic-pollution-sniffing-eco-dogs/.

Provisional U.S. Appl. No. 60/543,505, filed Feb. 11, 2004.

\* cited by examiner

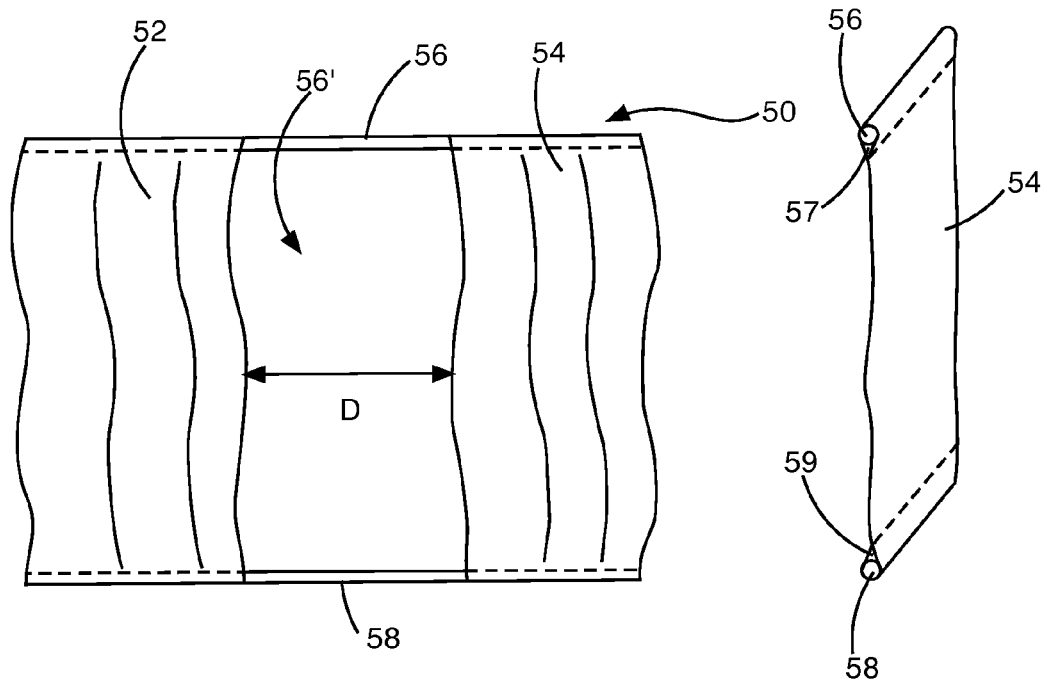
FIG. 2A
FIG. 2C
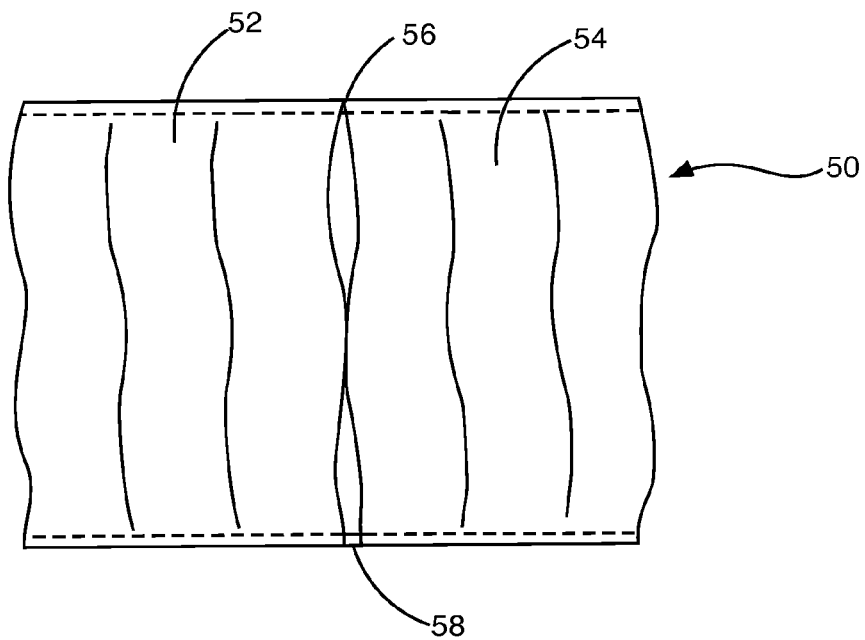
FIG. 2B

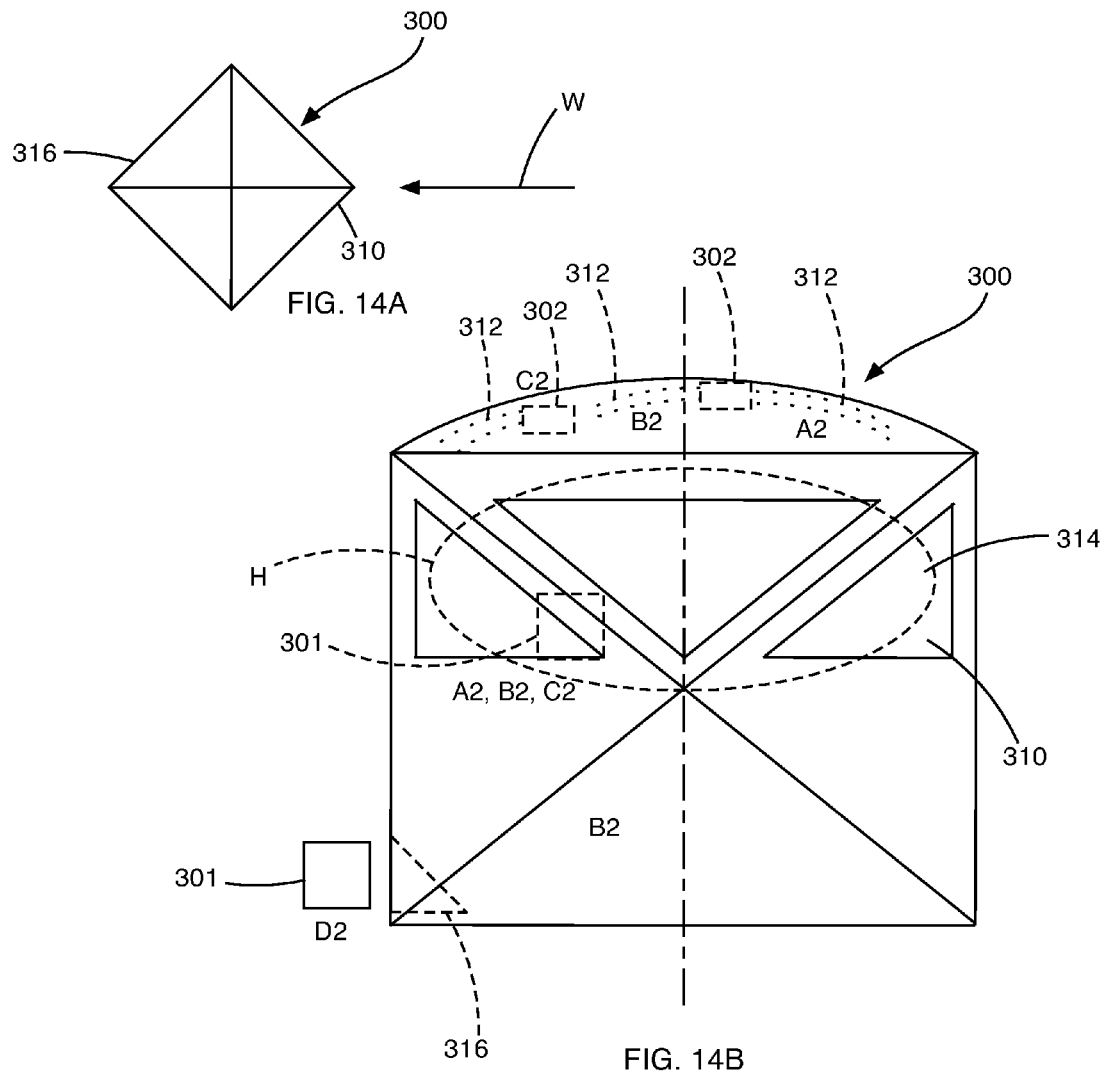

SYSTEM AND METHOD FOR REDUCING ODORS IN A BLIND

CROSS-REFERENCE TO RELATED APPLICATIONS

This application is a Continuation-in-part of and claims priority to U.S. patent application Ser. No. 12/660,347 filed Feb. 24, 2010, now U.S. Pat. No. 8,066,939, which is a division of U.S. application Ser. No. 11/714,083 filed Mar. 5, 2007, now abandoned, which is a continuation-in-part of U.S. patent application Ser. No. 11/018,620 filed Dec. 21, 2004, now U.S. Pat. No. 7,939,015, and of U.S. patent application Ser. No. 12/800,721 filed on May 21, 2010, which is a continuation-in-part of U.S. patent application Ser. No. 12/456,944 filed on Jun. 24, 2009, which is a continuation-in-part of U.S. patent application Ser. No. 12/326,240 filed on Dec. 2, 2008, which is a continuation-in-part of U.S. patent application Ser. No. 11/714,083 filed Mar. 5, 2007, now abandoned, which is a continuation-in-part of U.S. patent application Ser. No. 11/018,620 filed Dec. 21, 2004, now U.S. Pat. No. 7,939,015, said applications co-owned with the present invention and incorporated fully herein by this reference.

BACKGROUND OF THE INVENTION

1. Field of the Invention

The present invention is related generally to systems and methods for reducing perceptible odors, and more specifically to a system and method for using an ozone generator or similar device to prevent foreign scents from being detected by animals being hunted.

2. Description of Related Art

The prior art discloses a variety of devices and methods that purportedly reduce or masking detectable scents. Examples of such devices and methods are disclosed in U.S. Pat. Nos. 4,309,388; 4,867,052; 4,941,270; 5,087,426; 5,433,919; 5,468,454; 5,484,472; 5,514,345; 5,539,930; 5,547,476; 5,667,564; 5,681,355; 5,762,648; 5,766,560; 5,789,368; 5,790,987; 5,911,957; 5,931,014; 6,007,770; 6,009,559; 6,134,806; 6,134,718; 6,149,038; 6,156,268; 6,163,098; 6,284,204; 6,312,507; 6.355,216; 6,379,435; 6,503,547; 6,564,591; 6,565,805; and 6,576,190, and published U.S. patent application 2003/0044308—all of which are incorporated fully herein by this reference.

Hunters in particular have an interest in masking or eliminating their scent that could potentially alert game being hunted to their presence in the field. Game animals, such as deer and bear rely heavily on their sense of smell to react with their surrounding environment, including sensing danger, interacting with other animals and finding food. Scents that are not a natural part of the environment or that are associated with a food source will often function as a warning to such animals and often results in deterring the game animal from approaching a particular area when the foreign scent is detected.

According to Bernier et al. in Analytical Chemistry, 2000, volume 72, issue 4, pages 747-756 and references cited therein which are incorporated fully herein by reference, as many as 346 discernible compounds were identified in human skin emanations. The majority of these were carboxylic acids, alcohols and esters, but aldehydes, aromatics, heterocyclics, ketones, sulfides and thio compounds were also identified. Work cited in Bernier has identified over 100 compounds from human breath. Work cited in Bernier identified foot odor as another source of odor. Some of these compounds are the result of bacteria reacting with body emanations, while other compounds directly emanate from humans. Other compounds emanating from humans can include pheromones, deodorants and perfumes as well as the detergents, perfumes, scents, and additives left on human clothing. While it is not known which specific compound or blends of compounds emanating from humans are identified by an animal as human, there is currently no effective way to safely eliminate or reduce odors from humans and from clothing and equipment enough to reduce the odors to inhibit detection by game animals when a hunter or hunters are situated inside a hunting blind or other temporary structure employed to conceal visibility from animals.

Persons interested in preventing detection by animals of human odors or interested in attracting animals often use masks, attractants, or cover scents to prevent alerting and spooking the animal. Some commonly used masks are carbon sprays which, in addition to being dangerous to inhale and which can irritate skin, become ineffective once dry. Many attractants contain animal urine or estrous, which besides being offensive to the human user, have limited shelf life and are generally ineffective since, especially the estrous-based attractants, tend to occur naturally only in certain seasons. Cover scents, such as fruit extracts or fragrances, last for only a short time since they have a half-life in which the amount of cover scent diminishes over time if not reapplied. In addition, they are often so over-powering that the animal easily identifies the smell as unnatural. The use of descenting soaps and shampoos is messy, time-consuming, often skin irritating, often ineffective and does not address breath odor. Breath descenting using herbs is generally distasteful, and facemasks containing carbons or sieves are extremely uncomfortable.

More recently, the use of clothing containing activated carbons and/or clothing containing bacteria killing metals such as silver has gained some popularity. However, activated carbon has a very low capacity for odorants and requires temperatures preferably above 400° C. and more preferably above 600° C. to regenerate the carbon. These temperatures are well beyond temperature (100 C to 120 C) that a conventional gas or electric clothes dryer is capable of achieving. Placement of clothing in ovens capable of achieving 400 C plus temperatures needed to regenerate the carbon can damage the fabric of a garment. Silver or other metal-containing clothing requires direct contact of the metal with the bacteria to be effective, which is almost never the case since the clothing would then be so restricting as to be uncomfortable. These types of clothing are also expensive and do not address human odors such as those in human breath, nor do they address any of the odors emanating from the foot or any exposed part of the skin like the head and hands.

It has been discovered that gaseous ozone effectively kills bacteria and reduces or eliminates odors emanating from humans as well as odors contained in clothing worn by hunters. The advantages of ozone over other known masking and descenting methods include the facts that: ozone is a gas that eliminates odors emanating from a person (e.g., a hunter) and from personal equipment and can eliminate odors in a space between a person and an animal; and ozone is completely natural to the environment and leaves behind a very pleasant clean smell that wildlife and humans readily recognize, e.g. after a lightning storm. Known ozone generators include, but are not limited to, electrical discharge, UV light, radio wave and combinations thereof. The generator may be battery operated, operated with a car adaptor, and/or may be operated with AC current. The AC current may be supplied directly from an electrical outlet, or may be supplied using a portable generator.

Ozone has been described to treat odorous air, microorganisms, bacteria, mold, smoke, aromatic hydrocarbons, and volatile organic compounds (see for example U.S. Pat. Nos. 1,961,878; 2,203,188; 3,421,836; 3,750,556; 3,937,967; 3,949,056; 4,045,316; 4,863,687; 4,904,289; 4,990,311; 5,087,426; 5,835,840; 5,983,834; 6,094,549; 6,613,277; 6,632,407; 20020030022; 20060096331; and references cited therein, which are incorporated fully herein by this reference); and foreign references EP 261987; WO 200151096; WO 2003089017; WO 2005021135. WO 2005077425 and references cited therein, which are incorporated fully herein by this reference. In examples where clothing or personal effects are placed in a container, a portable enclosure, or a special descenting closet or room located, e.g., in a lodge or cabin in which the hunter is staying, as soon as the hunter leaves the building and enters a vehicle, or passes a moving vehicle, or begins to sweat, any prior descenting is of little value.

Animals have an acute sense of smell and are capable of recognizing a human scent or any other scent that is not advantageous in that environment at long distances. Moreover, game animals have an innate ability to detect individual scents when multiple scents are blended together that may not be detectable by humans. To avoid scent recognition and detection, a hunter will attempt to stay down wind of the animal being hunted. Certain known methods used by hunters to trick animals are to mask the human odor utilizing a carbon spray, cover spray scent or an animal scent. Unfortunately the animal scents which are utilized, are obnoxious and linger on the clothing for long periods of time and often do not mask out human scents. Some of the scents utilized include animal urine. A hunter who is camping overnight does not desire the animal scents to be carried over to bedtime, home, car, etc.

There are other drawbacks in utilizing animal scents or any other scents. The scent may attract a predator that the hunter may not be prepared to encounter. Containers containing food, beverages, or any other substance emit scents readily recognizable to animals that may not be masked by animal scents or may not be natural to a given environment. Female hunters can emit a readily recognizable scent to animals from menstruation that may not be masked by animal scents. Also, the weapon used by the hunter has an odor recognizable by some animals that cannot be disguised with a scent.

In the past, hunters have prepared their clothing before hand by washing to remove prior scents and/or human odor. The soaps used in washing clothing may, however, leave a detectable odor. Moreover, out in the field, the hunter will sweat and permeate the clothing with a human scent, making any prior washing ineffective.

U.S. Pat. No. 5,833,740 to Brais discloses an apparatus for sterilizing bottles utilizing ozone, the entirety of which is incorporated by this reference. The reference recognizes that ozone in large quantities can be harmful or irritating. Ozone is a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria. Catalytic ionization of air using ultraviolet light is known to produce a mixture of ozone-containing hydroxyl and hydroperoxide ions. Ionization devices that are used to eliminate smoke and odors, e.g. those used in automobiles, are known in the art to produce hydroxyl and hydroperoxide ions. Other oxidizing agents are also known in the art.

For safety reasons, government regulations have recommended, and sometimes regulated, the amount of ozone to which a human is to be exposed. For example, OSHA requires that employee permissible exposure limit (PEL) as an eight-hour time-weighted average value of 0.1 ppm ozone in air or a two-hour time-weighted average value of 0.2 ppm ozone in air. The OSHA short term exposure limit (STEL) is 0.3 ppm over a 15 minute period, not to be repeated more than two times in an eight hour period. Prolonged exposure of humans has produced no apparent ill effects at 0.2 ppm.

Consequently, it is desirable to provide a system and method for effectively removing or masking human scent while ensuring that a concentration of ozone within an at least partially enclosed structure is controlled to at or below acceptable levels.

SUMMARY OF THE INVENTION

A principal of the invention is to provide a system and method for effectively removing and/or masking human scent when a person is disposed within a temporary and partially enclosed structure, such as a hunting blind, in a safe manner. The present invention is directed to systems and methods for reducing or eliminating the various odors of one or more persons in a temporary structure, such as a hunting blind, through the use of ozone generating products to reduce or eliminate human odors that are detectable by animals. The invention relates to a system and method of significantly reducing or eliminating foreign scents that emanate from clothing, equipment and persons that are contained within and emanate from a temporary structure such as a hunting blind. This is accomplished by utilizing a device that generates ozone and/or a combination of hydroxyl and hydroperoxide ions within the temporary structure in a controlled manner to control the level of oxidant within the temporary structure to effectively eliminate foreign scents emanating from the temporary structure. This is systematically achieved by considering wind conditions, venting of the temporary structure and placement of the oxidant generator within the temporary structure. As such, regardless of the position of the temporary structure relative to the game animal being hunted, scent from the temporary structure can be effectively and safely controlled. The foreign scents may include, but are not limited to, any scent in a space between a human and an animal, such as scents emitting from human breath, human bodies, and from clothing and equipment, that are not native to the environment and/or that may disadvantageously cause an animal being hunted to avoid the area around the temporary structure.

The present invention, in certain aspects, is directed to systems and methods which use and oxidant, such as gaseous ozone, to kill bacteria and/or the odor produced from the breakdown of bacteria and reduce or eliminate odors emanating from humans, e.g. in breath or from skin, as well as odors in clothing worn by a person or equipment that are volatilized into the air space between the human and the wildlife to prevent wildlife from detecting the presence of humans and/or to enhance encounters with and the attraction of wildlife. One particular embodiment of the invention is directed to utilizing a portable ozone generator within a temporary structure, such as a tent or hunting blind erected in an open environment for concealing one or more persons and equipment situated within the structure. The ozone generator is employed to generate gaseous ozone within the temporary structure to reduce or eliminate game odors that would otherwise discourage the attraction of game animals for hunters or other forms of wildlife for wildlife enthusiasts and photographers.

In another aspect of the invention, a system and method is provided for deodorizing the air emanating from a temporary structure within which is housed the hunter, equipment and apparatuses of the hunter in an open environment and to descent the surrounding air emanating from the temporary structure. More particularly, there are provided systems and methods for masking, reducing or eliminating human scent or any other foreign scent emanating from clothing, equipment, supplies, the temporary structure itself that is volatized in the air within the temporary structure and that surrounds the temporary structure used by hunters during a hunt—through the use of ozone or hydroxyl and hydroperoxide ions produced by ionization in a manner that will not cause irritation or injury to the user or equipment within the temporary structure by controlling the amount of ionized particles within the temporary structure.

Yet another aspect of the invention is to provide a system and method for military personnel to escape detection by other humans or by scent animals (e.g., scent dogs). In certain particular aspects, the present invention provides systems and methods for reducing or eliminating human or any other foreign scent emanating from items, e.g. from clothing and equipment, used by military personnel positioned within a temporary enclosure desiring to evade detection or capture and from human odors in the surrounding air that result from body (e.g., perspiration and breathing), clothing or equipment emanating odors. This is accomplished through the use of ozone or ozone with hydroxyl and hydroperoxide ions produced by ionization in a manner that would not cause irritation or injury to the user or equipment by controlling the amount of ionized particles within the temporary structure.

In the various embodiments of the present invention, a human being is exposed to ozone generated by an ozone generator. In such embodiments, the human being may be exposed for a relatively short period of time (e.g., about 2 hours or less) to ozone in a time weighted average concentration of about 0.2 parts per million or less. In situations where a person is exposed to ozone for a longer period of time of up to about 8 hours or less, the ozone time weighted average concentration is limited to an average of about 0.1 parts per million or less. Thus, according to the present invention, an acceptable and effective level of ozone on a time weighted average to which the person or persons are exposed is maintained within the temporary structure at an ozone concentration level of 0.2 ppm or less for exposures that are about 2 hours or less and 0.1 ppm for longer exposures up to about 8 hours or less.

In certain embodiments according to the present invention, the temporary structure is pre-treated with ozone so that ozone is retained on the structure, e.g. for several hours and, in certain aspects, for up to 24 hours, and in other embodiments for more than 24 hours. Ozone retained on the temporary structure continues to provide a descenting effect for an extended period of time while a sufficient quantity of ozone is retained within the fabric of the temporary structure. A variety of fabric materials, including, but not limited to knits, cotton, cotton blends, other fibrous fabrics and coarse materials are capable of retaining ozone for a period of time. In addition, by forming the temporary structure from a permeable or semi-permeable fabric material, ozone generated within the temporary structure continue to provide descenting of the temporary structure as the ozone particles become entrapped within and/or pass through the fabric of the temporary structure.

The present invention thus, in one embodiment, provides a method and apparatus for controlling a concentration of ozone within a temporary structure. The method includes providing a substantially enclosed temporary structure. The temporary structure comprises a plurality of sidewalls and a roof that may be formed of fabric or from other flexible or more rigid materials known in the art of temporary structures. For certain temporary structures formed of fabric, a frame may be coupled to the plurality of sidewalls and the roof for supporting the sidewalls and the roof above a ground surface. A plurality of selectively openable and closeable upper windows is disposed in the sidewalls. A plurality of selectively openable and closeable lower vents is disposed in the sidewalls. The lower vents are disposed at a location proximate a floor of the temporary structure. An ozone generator is disposed within and coupled to the temporary structure. At least one of the plurality of upper windows in the sidewall facing a hunting direction is opened to allow the hunter to view the hunting area outside of the temporary structure. At least one vent in a sidewall opposite the open upper window is open to cause a flow of air within the temporary structure to be between the open upper window and the open lower vent. The ozone generator is activated to produce ozone particles within the temporary structure to intermix with odors present within the temporary structure and to descent the odors as the odors emanate from the temporary structure so as to be substantially non-detectable by animals present outside of the temporary structure. The ozone particles continue to intermix with the air emanating from the temporary structure to continue to eliminate odors as the air flows back into the surrounding environment. The upper windows and lower vents are open a sufficient amount to cause air to be blown by wind through the temporary structure to maintain a time weighted average concentration of ozone of between about 0.04 to 0.2 ppm with a time weighted average of between about 0.04 and 0.1 ppm for longer exposure times and a more ideal time weighted average of between about 0.05 and 0.09 ppm within the temporary structure in order to provide an effective amount of ozone within the blind to bind to and/or mask scent molecules, but that is at an acceptable level for the occupant of the temporary structure. In order to provide an effective and acceptable level of ozone within the temporary structure, the systems and methods of the present invention are directed to provide a time weighted average of about 0.08 ppm within the zone in which the head of the hunter is most commonly located for a period of eight hours or less.

In another embodiment, the plurality of vents each have a top edge that is below a bottom edge of the plurality of upper windows to prevent silhouetting through the temporary structure.

In yet another embodiment, the temporary structure forms a hunting blind where the sidewalls and the roof are formed from a camouflage fabric.

In another embodiment, each vent has an opening area that is less than an opening area of the at least one window in the opposite sidewall.

In still another embodiment, the ozone generator is orienting to emanate ozone in a direction of wind blowing outside of the temporary structure.

In yet another embodiment, the ozone generator is positioned above a hunter zone within the temporary structure.

In still another embodiment, the ozone generator is sized to be capable of maintaining a time weighted average ozone concentration within the temporary structure of between about 0.04 to 0.2 ppm with an average of between about 0.04 and 0.1 ppm and a more ideal time weighted average concentration of between about 0.05 and 0.09 ppm within the temporary structure.

In another embodiment, all other vents other than those directly opposite the open upper windows are closed.

In yet another embodiment, all other upper windows are closed except for windows directly opposite the open vents.

If the external wind speed is below about 5 mph, additional lower vents can be opened or the size of the opening of the open lower vent increased to decrease the ozone concentration within the temporary structure. Likewise, if the external wind speed is above about 5 mph, the open vent can be partially closed to increase the time weighted average ozone concentration the temporary structure to between about 0.02 to 0.2 ppm with an average of between about 0.04 and 0.1 ppm and a more ideal concentration of between about 0.05 and 0.09 ppm.

The advantages and characterizing features will become apparent from the following description of certain illustrative embodiments of the invention. The features and advantages of the present invention are set forth or will become more fully apparent in the detailed description that follows. Furthermore, the features and advantages of the present invention may be learned by the practice of the invention and will become apparent to one skilled in the art upon review of the description, as set forth hereinafter.

BRIEF DESCRIPTION OF THE DRAWINGS

The following drawings illustrate exemplary embodiments for carrying out the invention. Like reference numerals refer to like parts in different views or embodiments of the present invention in the drawings. Those of ordinary skill in the art will realize that the following description of the present invention is illustrative only and not in any way limiting. Other embodiments of the invention will readily suggest themselves to such skilled persons.

FIGS. 2A, 2B and 2C are front, side and perspective views of a selectably operable and closable window for a temporary structure in accordance with the principles of the present invention.

FIG. 14A is a top view of a temporary structure in relation to wind direction in accordance with the principles of the present invention FIG. 14B is a side view of the temporary structure shown in FIG. 14A.

DETAILED DESCRIPTION OF THE INVENTION

Figure 1:
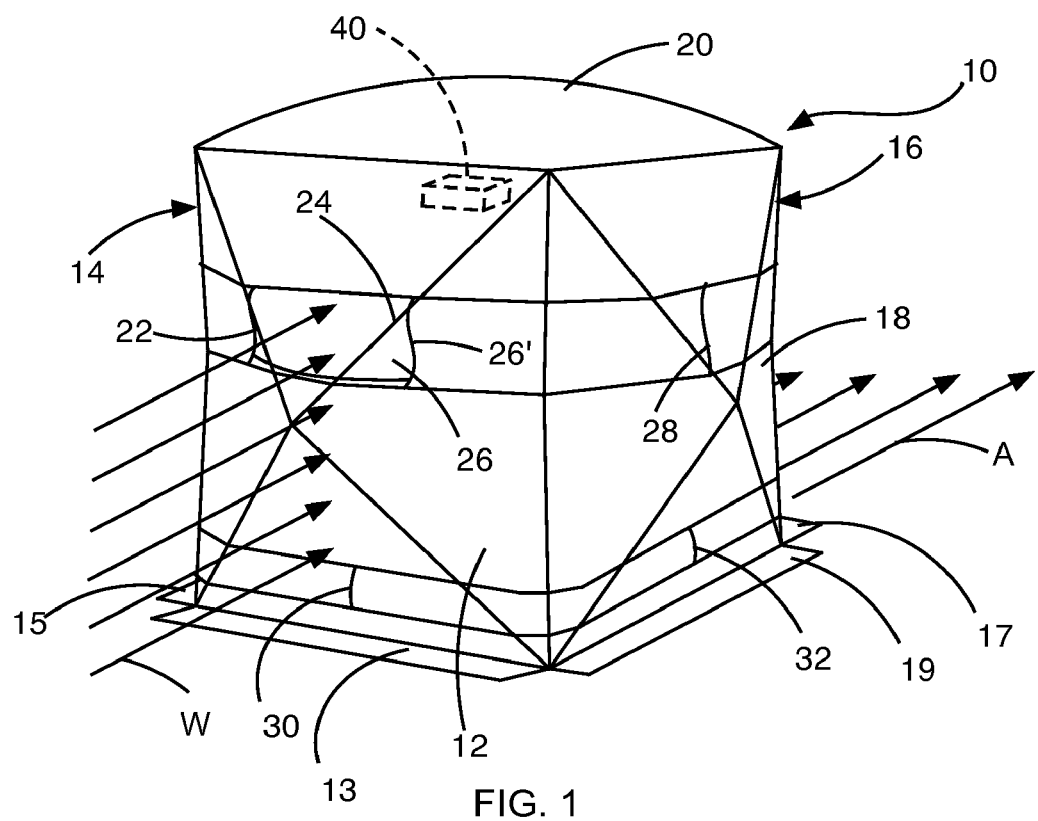
FIG. 1 is a perspective side view of temporary structure in accordance with the principles of the present invention.

Referring now to FIG. 1, there is illustrated a temporary structure in the form of a hunting blind, generally indicated at 10, in accordance with the principles of the present invention, "Temporary structure" as used herein includes any man-made place of observing, hiding and/or protecting a person including, but not limited to, a tent, blind, shack, tree stand, or other partially or fully enclosed structure for protection from natural elements or concealment, and combinations thereof, whether formed primarily of fabric or other flexible or rigid materials that can be assembled, disassemble and reassembled by one or more users. "Person" as used herein includes, but is not limited to, a "hunter" where a "hunter" is defined as including hunters of wild game and other animals and also includes nature enthusiasts, trappers, military personnel, military personnel seeking to evade others and/or avoid capture, hikers, fishermen and fisherwomen, backpackers, and photographers; and "hunt" or "hunting" is defined as including the hunting of wild game and other animals for the purposes of encountering, attracting, avoiding, escaping from, photographing, avoiding detection by, capturing, killing and/or observing them. "Animal" as used herein includes, but is not limited to, any small or large game animal including deer, elk, sheep, pig, moose, caribou, bird, rabbit, elephant, mountain lions, bear and fish, and combinations thereof and, in certain aspects, "animal" includes human beings. For example, a human may desire to prevent the detection of human body odors or odors resulting from the human consumption of various foods and/or spices (e.g., pepper or curry) and/or beverages by the human self or herself or by another human, "Hunter zone" as used herein defines the area within a temporary structure according to the present invention in which the head and/or upper torso or body of the hunter is typically positioned. This will most often be at a location within the temporary structure above the lower edge of the viewing window(s) or at or near chest level of the hunter and generally near the central interior area of the temporary structure, typically a space defined by a volume that is one to two feet from the outer walls of the temporary structure.

The hunting blind 10 is generally formed from a plurality of sidewalls 12, 14, 16 and 18 and a roof 20. The walls 12, 14, 16 and 18 and roof 20 are formed from a plurality of panels, which in the case of fabric panels may be sewn together. Of course, the side walls and/or roof panels may be formed from other materials known in the art of temporary structures, such as wood, plastic, polymer, composite materials and the like. The bottom sides of each wall 12, 14, 16 and 18 are provided with laterally extendable ground flaps 13, 15, 17 and 19, respectively, that can be secured to the ground with stakes (not shown) to limit air flow between the bottom of the blind 10 and the ground on which it is resting. Internal support structures, such as poles 22 and 24 provide a frame to support the walls 12, 14, 16 and 18 and roof 20 to form the hunting blind 10. The walls 12, 14, 16 and 18 of the hunting blind 10 are provided with a plurality of selectively openable and closeable windows, such as windows 26 and 28 and vents 30 and 32. The windows 26 and 28 are principally provided to allow a hunter positioned within the blind 10 to aim at and shoot a game animal from the window without being detected by the animal. "Hunt" or "hunting" is the searching of wild game and other animals for the purposes of encountering, attracting, avoiding, escaping from, photographing, avoiding detection by, capturing, killing and/or observing such wild game and other animals.

A secondary purpose for the windows 26 and 28 is to direct airflow through the blind 10 in a manner prescribed according to the principles of the present invention.

In order to eliminate or significantly reduce human or other foreign scents emanating from and being present around the hunting blind 10, an oxidizing gas generator 40 is situated inside the blind 10. "Descenting particle generators" include generators that produce an oxidizing particle that is capable of descenting human scents. The descenting particles include, but are not limited to, all applicable oxidants, such as ozone, hydroxyl radicals and hydroperoxides, and other known descenting particles that may be emitted from the generator with or without an operating integrated fan. Descenting particle generators of all sizes, weights, power sources and types are widely available from many sources. Optionally, the descenting particle generator may contain an additional on generator source for negative ionization of the air. These types of units are also commercially available. Optionally, the descenting particle generator can include the simultaneous or intermittent generation of other known oxidizing agents, bacteria and odor removing substances such as chlorine, zinc ricinoleate and/or cyclodextrine. For hunting purposes it may be desirable that the unit be lightweight, portable, and battery and/or solar power operated and/or with a hand crank generator. When hunting from within a temporary structure according to the present invention, such as blind or tent, if a portable generator or source of AC electric power is available, then descenting particle generators having this power receiving capability are also desirable. When hunting from a temporary structure according to the present invention, such as blind or a tent, it is still desirable to use low weight generators since the generator may be suspended from the roof of the temporary structure, but generators weighing up to about 8 lbs. and more may also be used. In general, light weight ozone generators produce lower levels of ozone and generate ozone for a shorter period of time, especially when small batteries such as size A, AA, AAA, C, D and 9 volt batteries are used. However, many battery-operated portable ozone generators last eight hours and more on one battery charge. The ozone generation source can be of any type including a UV lamp, electrical discharge, or combination of both. Certain portable, battery-operated and solar-operated ozone generators have UV lamps as the ozone generator source due mainly to the lower voltage required for UV lamps. Larger ozone generators capable of operating on AC current can be UV lamp, electrical discharge or a combination of both. Electrical discharge ozone generators can be capable of generating larger amounts of ozone in a smaller size container, but adding blowers, fans and transformers (which is within the scope of the present invention) can result in some generators being heavier than ozone generators having UV lamps. Small, portable battery and solar operated ozone generators are available which have small fans, though many have no fan at all. One advantage of including at least a small fan is that the ozone can be dispersed over a larger area more readily, but it is not necessary that a fan be included in the ozone generator. For ozonating a larger area within a blind, especially when two or more hunters are occupying the blind, an ozone generator having a fan or fan blower may be used, but not required. If a fan or fan blower is used, a fan can be used which makes minimum noise, especially beyond about a ten foot radius of fan operation so as not to alert a game animal to the presence of the blind or the hunters.

Certain ozone generators are capable of producing 1 mg and up to 5,000 mg/hr of ozone and more. For safety considerations, in certain embodiments of the present invention a person is exposed to a time weighted average concentration of 0.1 ppm ozone or less over an 8 hour time period or less: but exposures to larger concentrations up to about 0.2 ppm ozone and more over short periods of time (e.g. less than about 2 hours) is an acceptable exposure to humans. One desired ozone generator is one that can maintain a time weighted average concentration of about 0.1 ppm or less within a temporary structure within which one or more humans are positioned. In certain aspects the present invention provides systems and methods for reducing foreign scent emanating from an at least partially enclosed space and between a human being and an animal, the system and methods including generating descenting material with a generator, introducing the descenting material into the at least partially enclosed space and the space between a human being and an animal, the space containing foreign scent, and reducing or masking the foreign scent in the space with the descenting material. In certain embodiments, the descenting material is ozone and the method further includes: exposing the human being to a time-weighted average value of approximately 0.1 ppm ozone or less (e.g., 0.1 to 0.04 ppm) in air over a time period of eight hours or less within a temporary structure within which the human being is situated. In other aspects, the present invention provides a system and method for reducing and/or masking foreign scent in a space between a human being and an animal, the system and method including producing descenting material with a generator located within a temporary structure within which the human being is also situated, regulating and/or controlling the amount of ozone present within the temporary structure and reducing the foreign scent emanating from the temporary structure with the descenting material. Various factors will affect the amount of ozone required to be produced over time in order to provide effective foreign scent control. These factors include, but may not be limited to, the size of the temporary structure, the configuration of the temporary structure, the number of humans disposed within the temporary structure, external wind conditions, internal temperature within the structure, external temperature outside the structure, the ozone production capacity of the ozone generator and the position of the ozone generator within the temporary structure. Another factor that affects the amount of ozone required over time in order to provide effective foreign scent control is the resonance time of the ozone particles within the temporary structure. That is, the longer the resonance time within the temporary structure, the more time the ozone has to interact with odor producing particles before they exit the temporary structure. As such, in an enclosed or partially enclosed environment, an ozone generator that has a smaller ozone producing capability may be employed as compared to the ozone producing capability of an ozone generated that may be required in an open air environment. Thus, depending on the configuration of a particular temporary structure and ambient conditions, various r yodels of ozone generators may be employed. For example, battery operated ozone generators like the OZONICS HR-200 or HR-150 ozone generators may be employed in accordance with the principles of the present invention. Likewise, other larger or smaller ozone generators known in the art could be employed, whether battery operated or powered by an external electrical source, such as 110 volt AC power.

The use of ozone can quickly reduce, mask or eliminate foreign scents emanating from a person or his or her clothing and equipment and in the space between the person and an animal. The ozone is cleanly reduced to oxygen. The many uses of ozone that are known to kill bacteria, eliminate smoke and react with alcohols, esters, saturated organics, acyclics, aromatic, heterocyclics and more to purify the air for healthier human consumption are used in certain systems and methods according to this invention not to purify the air for human breathing, e.g. for a hunter and his or her equipment normally in a very dean outdoor environment, but to react or otherwise interact with odors emitted by humans and their equipment so that these volatiles are not detected by an animal, e.g. a bear. Since ozone has a half-life of 20 minutes or more, airborne unreacted ozone still continues to interact with bacteria, byproducts of bacteria, odors and/or cloth rig. In addition, any gear that emits a foreign scent that is exposed to a sufficient concentration of ozone will cease to produce a detectable foreign scent. Without being bound by any theory, it is believed that in one aspect, ozone in the air kills bacteria and/or interacts with odor producing byproducts of bacteria in certain body areas, including, but not limited to, in the underarm and groin areas that are responsible for producing many of the odor-causing volatiles emitted by humans; and in another aspect, any volatile odors that are produced and emitted directly by humans via the skin or by breathing are oxidized by the ozone into compounds that are much less volatile and therefore far less detectable to animals, e.g. bear. In another aspect, it is believed that any volatile odors that are produced and emitted directly by humans via the feet and escape through the shoe or socks are oxidized by the ozone into compounds that are much less volatile and therefore far less detectable to animals. In yet another aspect, it is believed that the more powerful (but much shorter life-time) hydroxyl and/or hydroperoxide radical oxidants that are produced by ozone reacting with ultraviolet rays of the sun and/or the UV lamp of an ozone generator and/or moisture in the air contribute to odor elimination.

In yet another aspect, it is believed that any pheromone or combinations of pheromones (which contain a wide variety of alcohol, ester, and saturated organic functionality) that are produced and emitted by humans at levels far too small to be detectable by humans but not by animals, are oxidized by the ozone into compounds that are much less volatile and therefore far less detectable to animals. In yet another aspect, it is believed that odors from breath, such as aldehydes, alcohols and acids, are oxidized by the ozone into compounds that are much less volatile and therefore far less detectable by animals. In yet another aspect, it is believed that it is possible that oxidized volatiles, even if they are still somewhat volatile and detected by animals, are changed enough in composition that the animals no longer detect the oxidized volatiles as human.

In yet another aspect, it is believed that it is possible that higher levels of ozone in the environment around animals overpowers any human volatile such that the animals misperceive the higher concentration of ozone as the result of naturally-occurring phenomena that they do not associate with a foreign scent, such as scents produced by lightning.

There is no limitation to the number of ozone generators used except for taking the precaution of not allowing a person to be exposed to unsafe concentrations of ozone that are deemed unacceptable by current regulatory standards. For cost, convenience and safety, one ozone generator located within the temporary structure is sufficient for a temporary structure that is in the configuration of a conventional hunting blind capable of housing one or two hunters. Multiple generators located within the structure or outside the structure and combinations thereof, may produce additional foreign scent reducing benefits for larger structures, The ozone generator or generators may be, in one aspect, located at various heights within the temporary structure, depending on the size and configuration of the structure and external conditions such as temperature and wind speed. Thus, it is within the scope of the present invention to locate an ozone generator at a person's feet, above the person's head or near any part of a person's body. As will be described in more detail, the position of the ozone generator or generators within the temporary structure can affect the quantity of ozone present within the temporary structure as well as the resonance time of ozone particles within the temporary structure to reduce or eliminate odors emanating from the temporary structure.

Likewise, the generator 40 could be a device that produces ionization with UV light to generate hydroxyl and hydroperoxide ions. Hydroxyl and hydroperoxides are produced in a process known as "Radiant Catalytic Ionization" which utilizes ultra violet light that activates a photocatalytic target. In the case of an ozone generator, the generator 40 produces sufficient ozone to interact with odor emitting particles, substances and objects to fully or substantially descent such particles, substances and objects so that the odor is not readily detectable by a game animal being hunted. While the ozone generator 40 may include controls to regulate the amount of ozone generated, it is generally the case that ozone generators 40 are configured to produce ozone in a set quantity per hour (e.g., 200 or 450 mg/hr). As such, once the generator is activated, it will continue to produce ozone at the preset amount regardless of the amount of ozone present in the immediate vicinity. In a substantially fully or even partially enclosed space, such as the hunting blind 10, the concentration of ozone within the blind 10 can either exceed safety limits or be ineffective in eliminating foreign scents unless the proper ozone generator is employed and properly used and the blind is configured to allow selective control of the ozone concentration according to the principles of the present invention.

As further illustrated in FIG. 1, when using the blind 10 in an open air environment, such as when used in the field for hunting game animals, the hunter will typically position the blind 10 downwind from where the hunter expects a game animal to be present. This is to cause any foreign scents from the blind 10 to be carried by the wind, represented by arrows W, away from the area being hunted. "Foreign scent" is a scent or odor that is not natural to the particular environment, and may include, but is not limited to, human body odor, human breath odor, odors from volatiles and contaminates and odor that may emanate from any equipment, supplies or clothing. The generator may produce an oxidizing gas, namely, ozone. In such a situation, the window 26 may be open for allowing a hunter positioned within the blind 10 to view the hunting area. As the wind W approaches the blind 10, some of the air will enter the blind 10 through the window 26. The amount of air entering the blind 10 is dependent upon the square area of the window opening 26' and the square area of any vent openings that will allow the air entering the blind 10 to escape from the blind 10. Thus, the blind 10 is provided with selectively openable and closable vents proximate the bottom edged of each side wall 12, 14, 16 and 18 that will allow air entering the blind 10 to move through the blind 10 and escape through one or more open vents. When the air passes through the blind 10, it becomes intermixed with ozone from the ozone generator 40 and any foreign scents within the blind 10. By situating the vents, such as vents 30 and 32 along an indirect path of the wind W, a certain resonance time of the ozone and air within the blind is maintained. That is, because the air enters the window 26, which is located in an upper portion of the blind 10 and is allowed to exit the blind 10 through a vent in a lower portion of the blind 10, the air and ozone will intermix for a period of time within the blind 10 before exiting as indicated by arrows (A). In general, the window 26 that is facing in the direction of wind W will be open and one or more vents located oppositely from the window 26 will be opened to direct the flow of air through the blind from an upper portion to a lower portion before the air A leaves the blind 10. As will be described in more detail, the square area of the window opening 26' can be adjusted to allow more or less air into the blind depending on wind speed of the wind W. Also, adjusting the square area of the vent openings can also help to increase or decrease the flow of air A through the blind and effectively alter the resonance time of the air and ozone interaction within the blind.

Once the blind 10 is erected and the ozone generator is activated and operated for a period of time, the hunter can use an ozone detector to determine the amount of ozone present within the blind 10 and then make adjustments to the window and/or vent openings in order to increase or decrease the ozone concentration within the blind. This can be accomplished by using one of the various ozone detection systems or products known in the industry. Alternatively, based on the approximate internal volume of the blind 10, the size and position of the ozone generator within the blind and the approximate speed of the wind W, the hunter can adjust the window and vent openings to control the amount of ozone that remains within the blind 10 at any given time. Because of the expense of ozone detection systems, the process for determining ozone concentration based on wind speed and blind configuration is highly desirable and produces similar results to actual ozone detection systems.

As shown in FIGS. 2A, 2B and 2C, a window or vent 50 of a blind may be comprised of fabric panels 52 and 54 that are fastened around elastic cords 56 and 58. The top and bottom edges of each fabric panel 52 and 54 are looped around the respective elastic cord 56 and 58 and sewn to the respective panel 52 and 54 to form channels 57 and 59 (see FIG. 2C). The channels 57 and 59 that are formed along the top and bottom edges of each fabric panel 52 and 54 allow the fabric panels 52 and 54 to slide along the elastic cords 56 and 58. As shown in FIG. 2A, the fabric panels 52 and 54 can be slid along the cords 56 and 58 in a direction away from each other to form a window or vent opening 56'. The area of the window or vent opening is determined by the distance between the cords 56 and 58 and the distance D between fabric panels 52 and 54. In order to substantially or completely close the window or vent 56, the closest vertical sides of the fabric panels 52 and 54 are brought together as shown in FIG. 2B. The elastic cords 56 and 58 and associated fabric panels 52 and 54 are wrapped around the blind at a location where lateral openings in the blind are provided. In order to provide a plurality of such windows or vents around the entire blind, the cords 56 and 58 may circumscribe the entire blind with the upper cord 56 being positioned proximate an upper edge opening in the blind and the lower cord 58 being positioned proximate a lower edge opening. Additional fabric panels are similarly attached to the cords 56 and 58 so that at least one window or vent opening can be formed on each side of the blind. In the case of a blind of generally cylindrical construction, window or vent openings would be provided at approximately 90-degree increments so that at least four windows or vents could be formed. In a generally triangular prism shaped blind having three sides, window or vent openings would be provided on each of the three sides. It is further contemplated that the windows and vents of the present invention could include various configurations of flaps that are secured by hook and loop fasteners and/or zippers. Thus, the foregoing description of window and vent openings and closures therefore are provided by way of example and not limitation.

Thus, the lower vents provided in the blind, such as vents 30 and 32 shown in FIG. 1, may be configured in a similar manner to the window or vent 50 shown in FIGS. 2A-2C. The primary difference for a vent may be that the distance between cords 56 and 58 for vents may be closer together than for windows (e.g., 12 to 36 inches apart for windows and 2 to 12 inches apart for vents).

Figure 3:
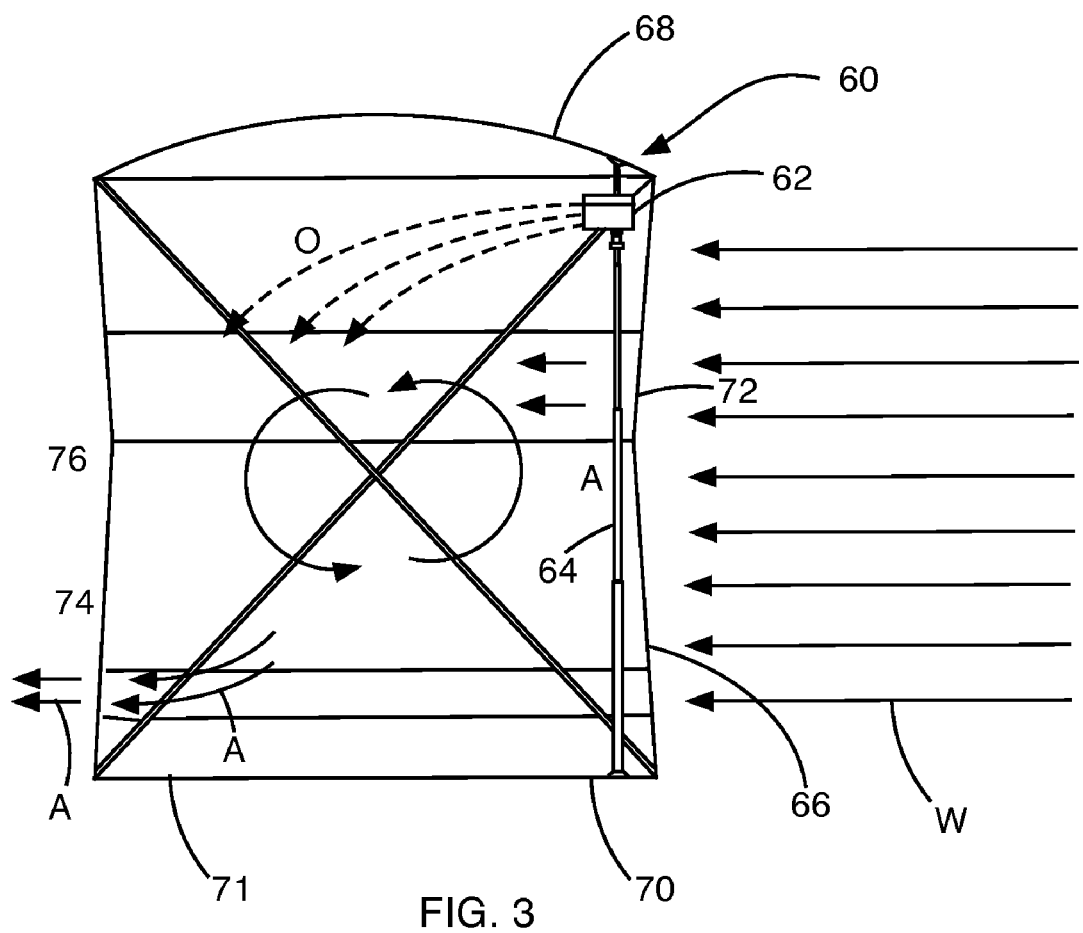
FIG. 3 is a side view of a temporary structure containing a descenting particle generator in accordance with the principles of the present invention.

Referring now to FIG. 3, there is illustrated a cross-sectional side view of a hunting blind, generally indicated at 60, in accordance with the principles of the present invention. The hunting blind 60 has a configuration similar to the hunting blind 10 illustrated in FIG. 1. Within the blind 60, an ozone generator 62 is mounted to a vertical extension pole 64 that is positioned within the blind 60 nearest the sidewall 66 of the blind 60 facing the wind W. The pole 64 may be of a telescopic configuration having releasably locking sections, similar in configuration to the legs of a camera tripod. Thus, the pole 64 can be extended to fit between the roof 68 of the blind and the ground 70 to provide a relatively rigid vertical support for mounting the ozone generator 62. In this example, the ozone generator is mounted proximate a top end of the pole 64 so that the ozone generator 62 is positioned near the roof 68 of the blind 60. In addition, the ozone generator 62 is oriented so that ozone produced by the ozone generator 62 is directed toward the center of the blind 60, i.e., away from the sidewall 66. A window 72 formed in the sidewall 66 allows air A from wind W to be blown into the blind 60. As the air A enters the blind 60 it is intermixed with ozone particles O produced by the ozone generator 62. As the ozone particles O and air A are intermixed within the blind 60, the ozone particles O will interact with any odor producing particles in the air as well as on any surface or substance that the ozone particles contact, such as clothing worn by a hunter, perspiration on the hunter's skin, equipment of the hunter located within the blind 60, etc. As air A continues to enter the blind 60 the air A is directed through the blind 60 along an indirect path that starts at the window opening 72 and ends at the vent 74 in the lower portion of the opposite side wall 76. Because the ozone O has a higher molecular weight than air (i.e., 48 for ozone compared to 42 for air), the ozone O will tend to settle downwardly within the blind. As fresh air A enters the blind and picks up odor particles, the naturally downward flow of ozone particles O will move through the air A contacting particles collected by the air A effectively descenting the air. In addition, as the air A circulates the ozone particles O through the blind, any surfaces or objects contacted by the ozone particles O will become descented in a similar manner. The descented air A is then allowed to vent through the vent opening 74 to the atmosphere.

The positioning of the vent 74 at a location that is not directly across from the window opening 72 has several benefits. First, by positioning the vent 74 near the bottom or floor 71 of the blind, air A entering the blind 60 through an upper window 72 will mix with the ozone particles O for an extended period of time to create a resonance time of the ozone particles O within the blind to generate greater a greater descenting effect. Furthermore, positioning the vent 74 at a position that is at a location away from the window 72 and not directly in line sight with the window 72 has an additional benefit related to concealment of a hunter positioned within the blind. When openings in the blind 60 are positioned directly across from each other, as would be the case if a window directly opposite the window 72 were opened in side wall 76, a condition commonly referred to a "silhouetting" can occur. That is, the profile of the hunter within the blind can become visible as light from the opposite window passes through the blind 60 to the window 72. An animal that looks at the blind 60 would effectively see a shadow outline of the hunter within the blind 60 which would likely alert the animal to the presence of the hunter. By positioning the vents at a vertical location that is substantially below the lower edge of the window 72, the possibility of such silhouetting to occur is significantly reduced if not completely eliminated.

Figure 4:
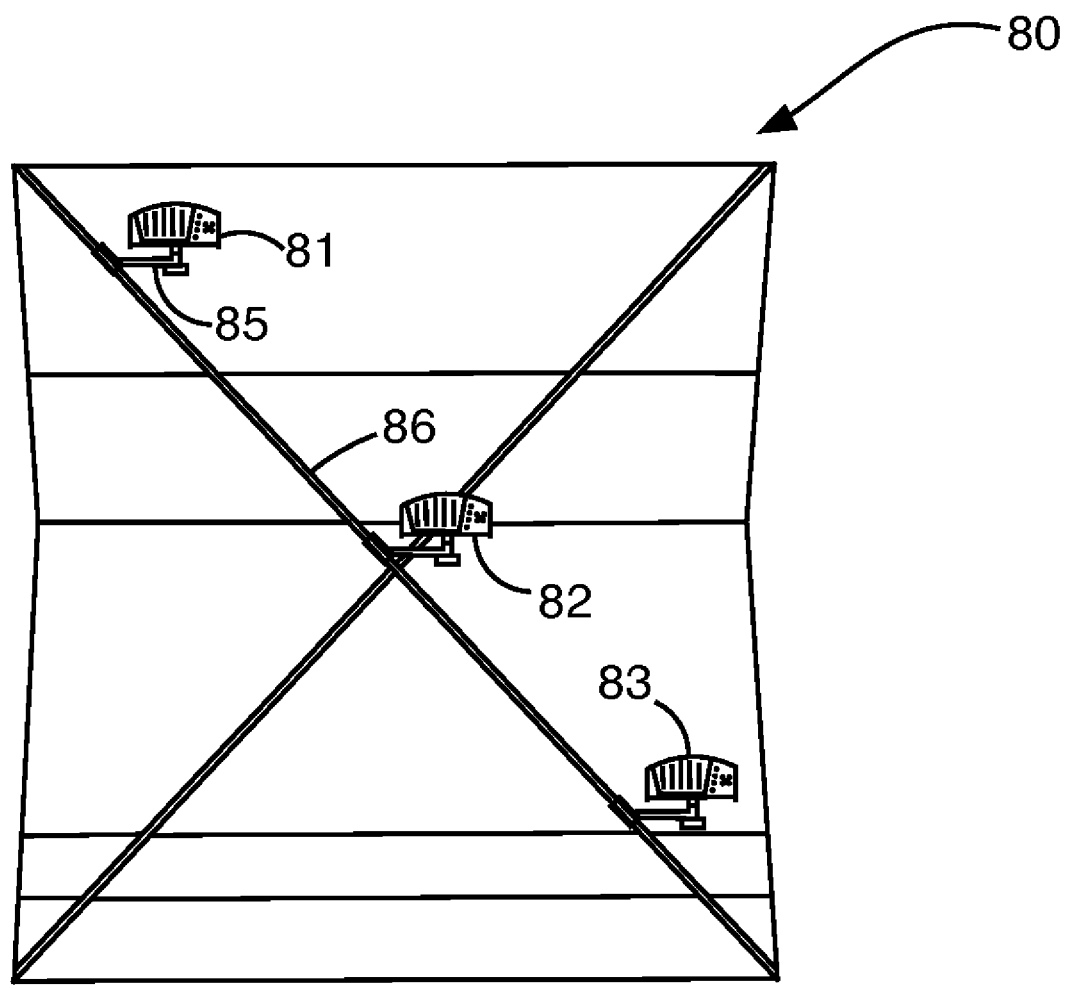
FIG. 4 is a side view of an inside of a temporary structure with a plurality of descenting particle generators positioned in a temporary structure in accordance with the principles of the present invention.
Figure 5:
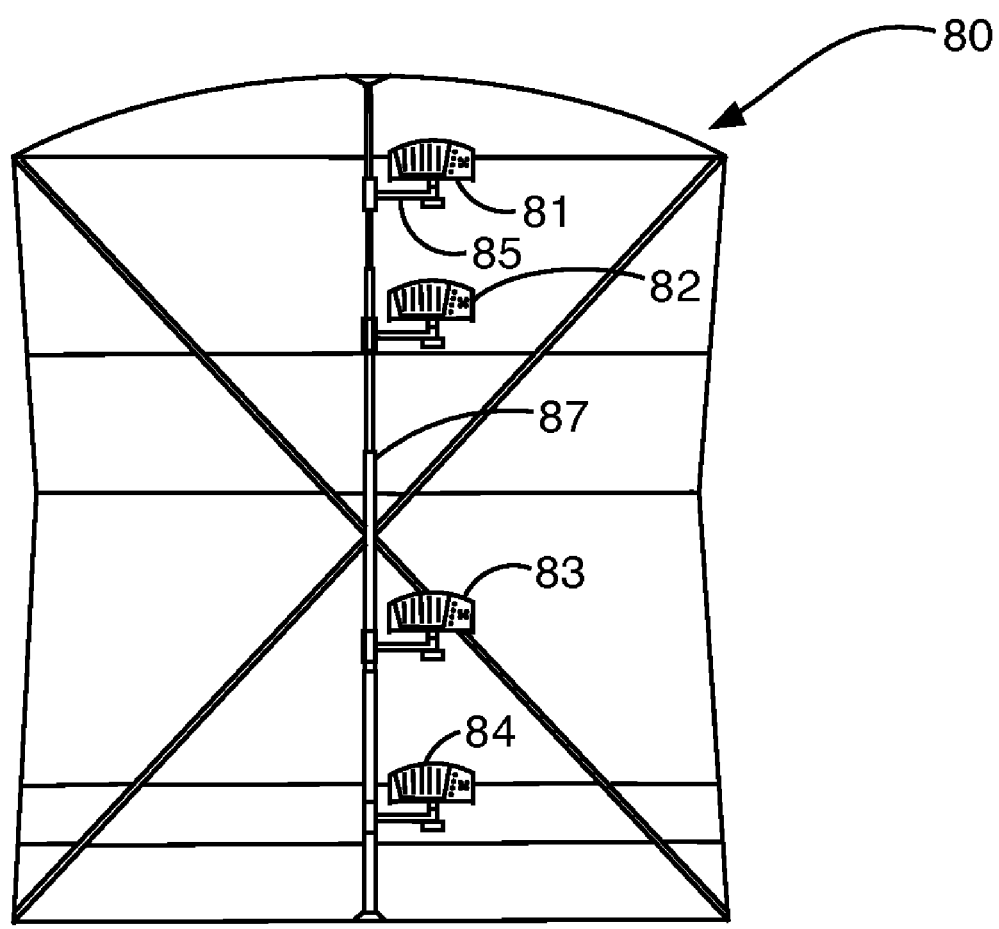
FIG. 5 is a side view of an inside of a hunting blind with a plurality of descenting particle generators positioned in a temporary structure in accordance with the principles of the present invention.

As shown in FIGS. 4 and 5, one or more ozone generators 81, 82, 83 and 84 may be used within a hunting blind 80. In addition, the ozone generators 81, 82 and 83 may be provided with various mounting hardware, such as mounting bracket 85, to mount the ozone generators 81-84 to a frame 86 or support member 87 of the blind 80 at various height locations within the blind 80. Thus, the present invention is not in any way limited to the configuration or construction of the blind 80 so long as one or more ozone generators can be mounted within the blind at a prescribed height and location in order to control the amount of ozone present within the blind 80 during operation of the ozone generator(s).

Figure 6:
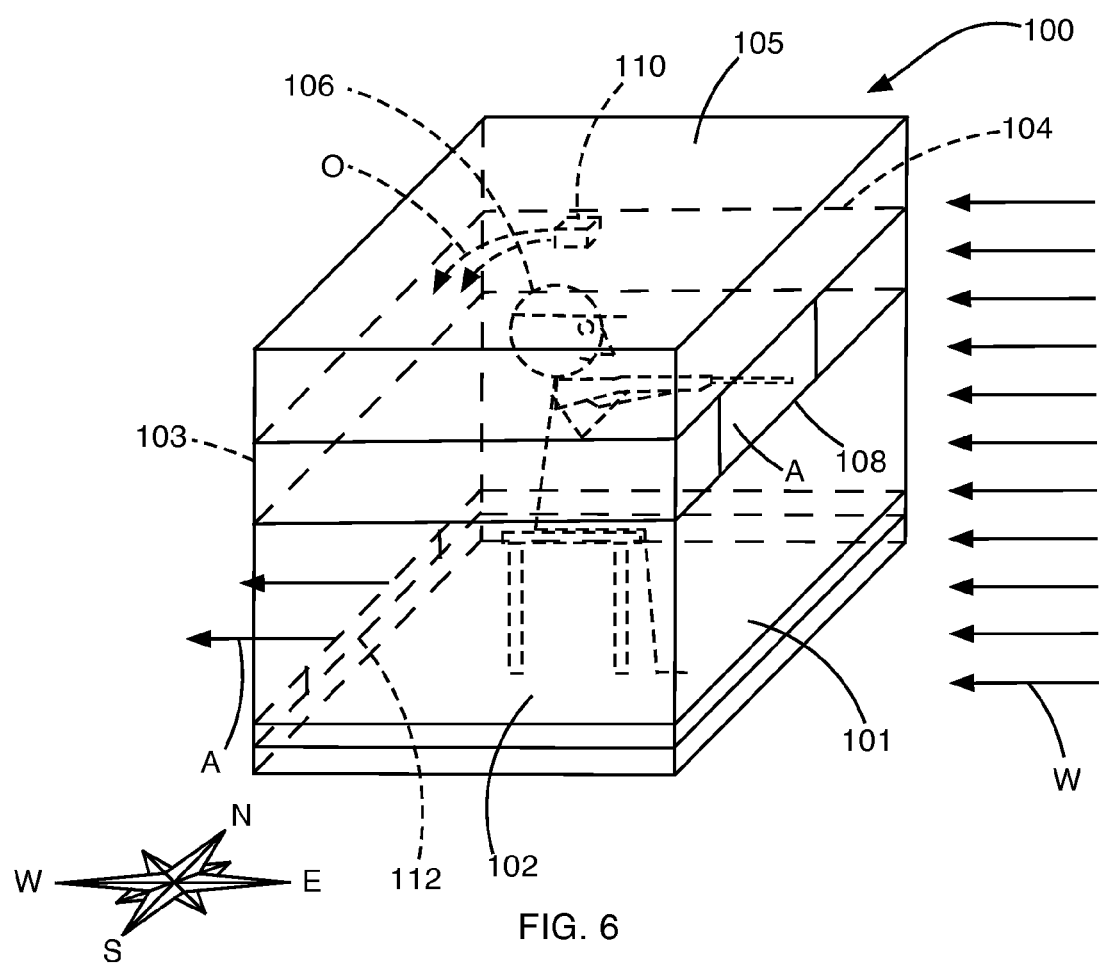
FIG. 6 is a side perspective view of a hunting blind with a hunter and ozone generator positioned within the hunting blind in accordance with the principles of the present invention.

Referring now to FIGS. 6-9, there are illustrated various blind configurations and ozone generator positions that may be employed, in accordance with the principles of the present invention, in order to control the amount of ozone maintained within the blind at any given time depending on external ambient conditions, such as wind direction and speed. As shown in FIG. 6, a blind 100 is comprised of four sidewalls 101-104 and a roof 105. A hunter 106 is positioned within the blind 100 and is facing the window opening 108 formed in sidewall 101. An ozone generator 110 is positioned above the hunter 106 and is oriented to direct ozone O in a downwind direction and away from the window opening 108. The side wall 101 is facing in the direction of the wind W so that air A from the wind W enters the blind 100 through the window opening 108 intermixes with the ozone O, and passes over and behind the hunter 106. This increases the possibility that the ozone O will descent odors emanating from the hunter and any associated equipment, such as a rifle, clothing, chair, etc. while keeping ozone O from being emitted over and around the face of the hunter. This effectively lowers the ozone concentration within the hunting zone of the hunter while maximizing interaction with odors that emanate from the hunter before the ozone and scented air A leave the blind 100.

A vent opening 112 is provided in the sidewall 103, which is the sidewall opposite the sidewall 101. In some blind configurations, the sidewall 101 may be considered the front wall and the sidewall 103 may be considered the back wall. In such cases, the blind 100 is positioned in the field so that the prevailing wind W (in this example, wind W moving from East to West) first contacts the front wall 101 so that the air A is directed through the blind 100 from the front wall 101 to the back wall 103. As the air A passes through the vent opening 112, the air A is sufficiently permeated with ozone O to eliminate any odor in the air A that leaves the blind 100.

Figure 7A:
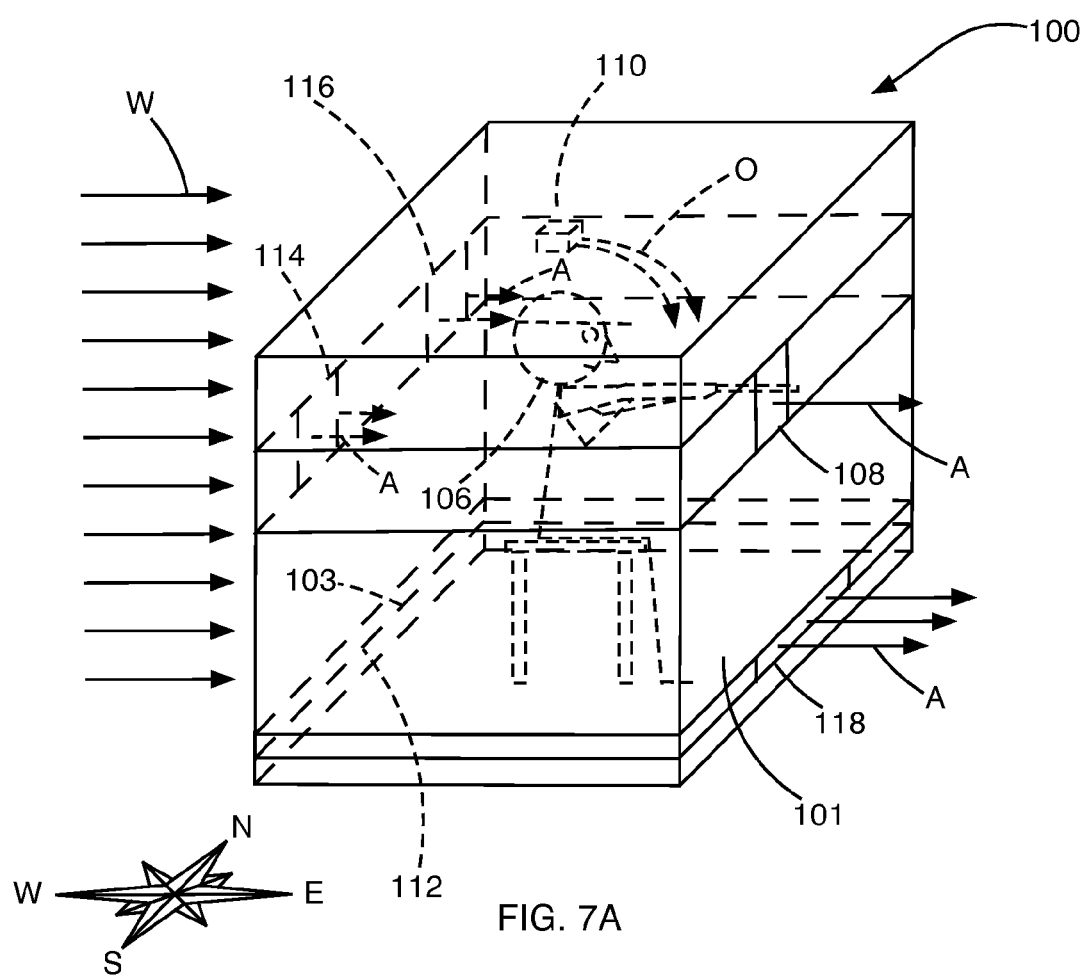
FIG. 7A is a side perspective view of a hunting blind with a hunter and ozone generator positioned within the hunting blind in accordance with the principles of the present invention.
Figure 7B:
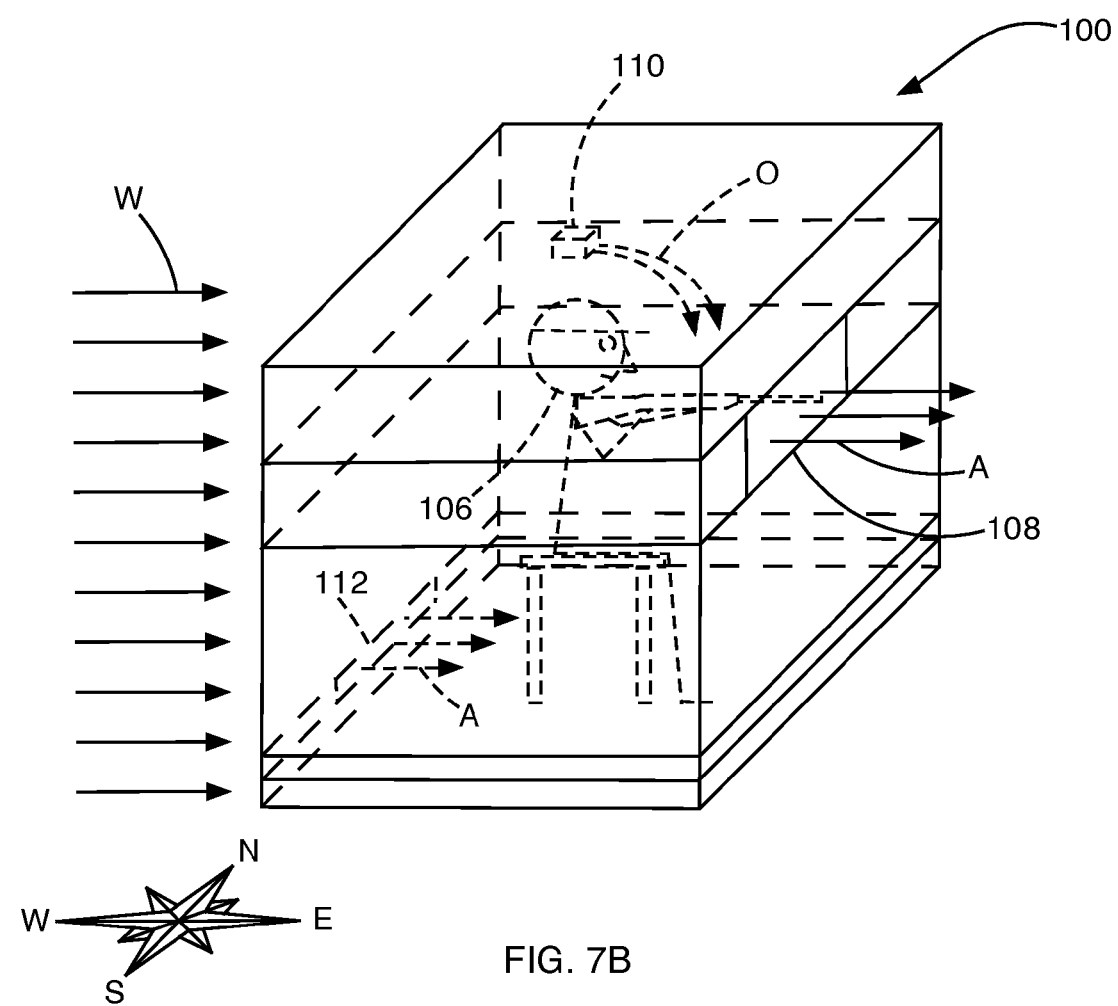
FIG. 7B is a side perspective view of a hunting blind with a hunter and ozone generator positioned within the hunting blind in accordance with the principles of the present invention.

As illustrated in FIGS. 7A and 7B, it is sometimes the case during a hunt that the wind W will shift directions. Thus, while the blind 100 was originally positioned with the wind coming from the East as shown in FIG. 6, the wind W is now coming from the West and contacting the back side 103 of the blind. In such situations, it is generally not often practical to move the blind 100 to a location where the hunter's primary hunting field is in view with the wind W in the direction of the front wall 101. Rather, the windows and vents of the blind 100 can be quickly reconfigured to maintain adequate ozone O concentration to descent air passing through the blind 100, while still allowing the hunter to view the primary hunting area and eliminate potential silhouetting. This can be accomplished in one of two ways. As shown in FIG. 7A, two smaller windows 114 and 116 can be opened in the wall 103. This will allow air A to enter through the windows 114 and 116. The window 108 in the wall 101 can then be narrowed to omit the amount of air A that can pass through window A. In addition, vent 118 is opened in the lower portion of wall 101 to allow the remaining air A to pass through the wall 101. The windows 114 and 116 are offset from being directly across from the window 108 to limit silhouetting with all three windows 114, 116 and 108 being more narrowly configured to reduce such a condition while still allowing the hunter 106 visibility through the window 108. Positioning the ozone generator 110 above the hunter 106 and directing the flow of ozone O toward the window 108 will permeate the air A escaping through window 108 with ozone O so that such air A is descented as it leaves the blind 100. Any remaining air A that exits through vent 118 will have had sufficient the within the blind 100 to be descented by the ozone O prior to such exit. As shown in FIG. 7B, configuring the blind 100 in a manner consistent with the blind configuration shown in FIG. 6 will also work. In this example, the air A from wind W can enter the blind 100 through the vent opening 112, intermingle with ozone O from the ozone generator 110 and exit through the window 108. In order to increase resonance time of the ozone O/air A interaction, the area of the vent opening 112 may be slightly larger than the area of the window opening 108 in order to create a slightly positive pressure within the blind 100 to allow sufficient mixing of the ozone O with the air A prior to exiting the blind 100. Again, positioning the ozone generator 110 above the hunter 106 ensures that sufficient amount of ozone O will be present within the air A as it exits the blind 100.

Figure 8:
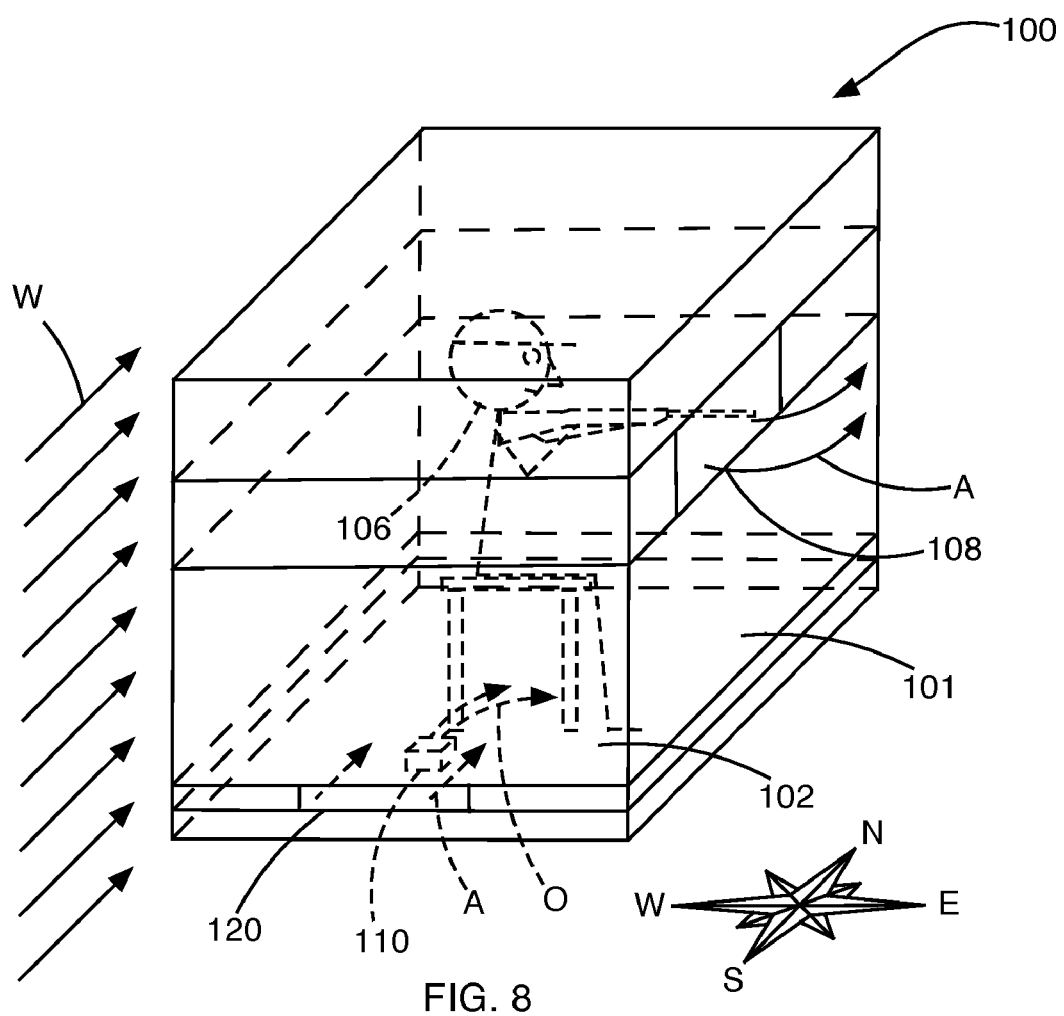
FIG. 8 is a side perspective view of a hunting blind with a hunter and ozone generator positioned within the hunting blind in accordance with the principles of the present invention.

As shown in FIG. 8, when wind conditions change so that the wind is primarily coming from the South while the primary hunting direction is to the East, a lower vent 120 can be opened in the sidewall 102. This will allow air A from the wind W to enter into the bottom of the blind 100 circulate throughout the blind 100 and exit through the open window 108 in side wall 101. Positioning the ozone generator 110 directly over the vent 120, either slightly above as illustrated or well above (e.g., near the midpoint or top of wall 102) will provide sufficient ozone O at a location near the incoming air A that will allow sufficient permeation of the ozone O into the air A and adequate resonance time before the air A exits the blind 100 through the window 108.

Figure 9:
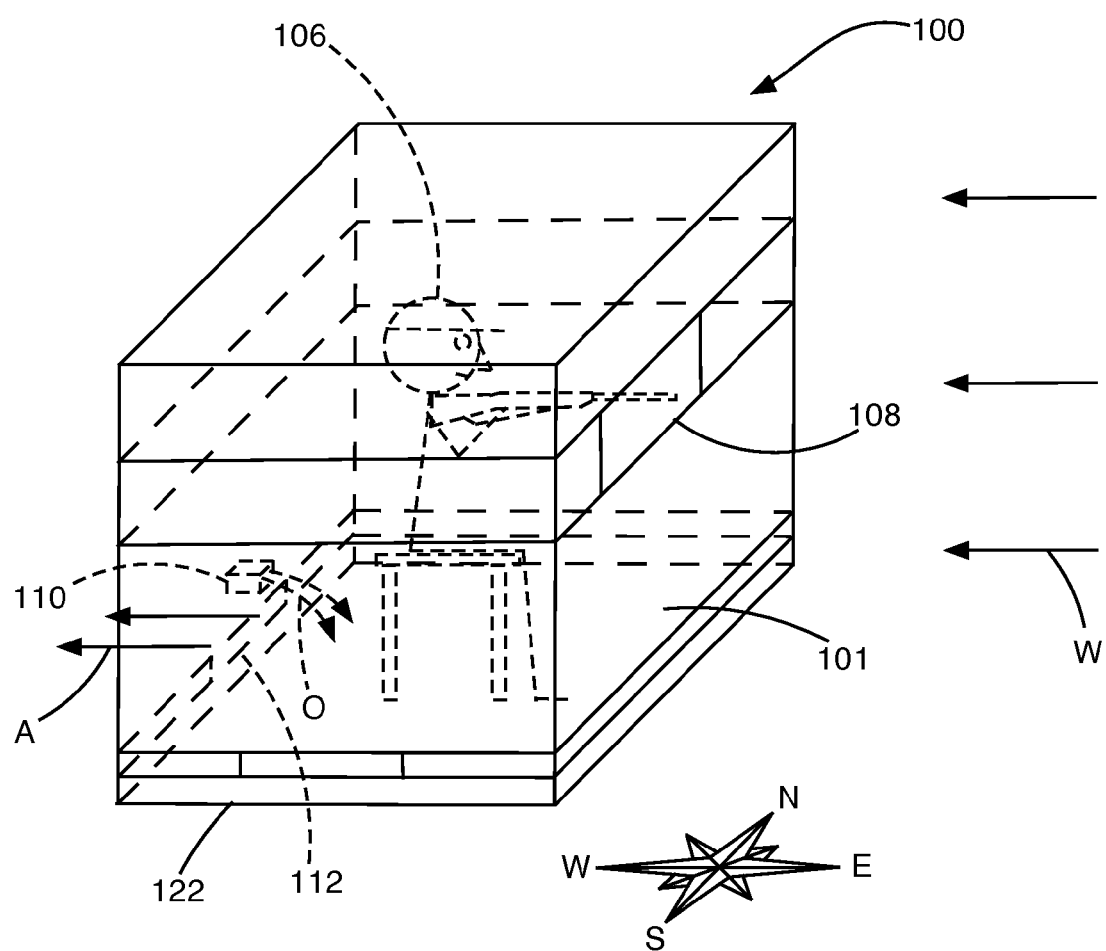
FIG. 9 is a side perspective view of a hunting blind with a hunter and ozone generator positioned within the hunting blind in accordance with the principles of the present invention.

In any of the foregoing situations when the wind speed of wind W decreases or is of a relatively low velocity (e.g., less than 5 mph), ozone O generated by the ozone generator 110 will not be essentially flushed from the blind 100 as rapidly as when higher wind conditions exist. As such, any ozone O produced will tend to linger within the blind 100 for a longer period of time. Thus, the resonance time of an ozone particle within the blind 100 will automatically increase. As such, the amount of ozone 0 within the blind can be regulated by positioning the ozone generator 110 closer to the floor of the blind 122. Because ozone 0 will tend to accumulate near the floor 122, any air entering window 108 will necessarily have to move to near the floor 122 before it can exit through the vent 112 located in the wall 103 as shown in FIG. 9. In addition, even if higher concentrations of ozone O exist within the blind 100 that what is generally deemed acceptable, such higher concentrations will be limited to the floor area of the blind 100 and away from the head of the hunter 106 in the upper portions of the blind 100 where breathing occurs. Thus, by raising or lowering the ozone generator 110 based on wind speed, in combination with the opening of certain windows and vents, the amount of ozone O within the blind can be effectively controlled to ensure safe operating conditions while substantially eliminating odors that would otherwise emanate from the blind 100.

Figure 10:
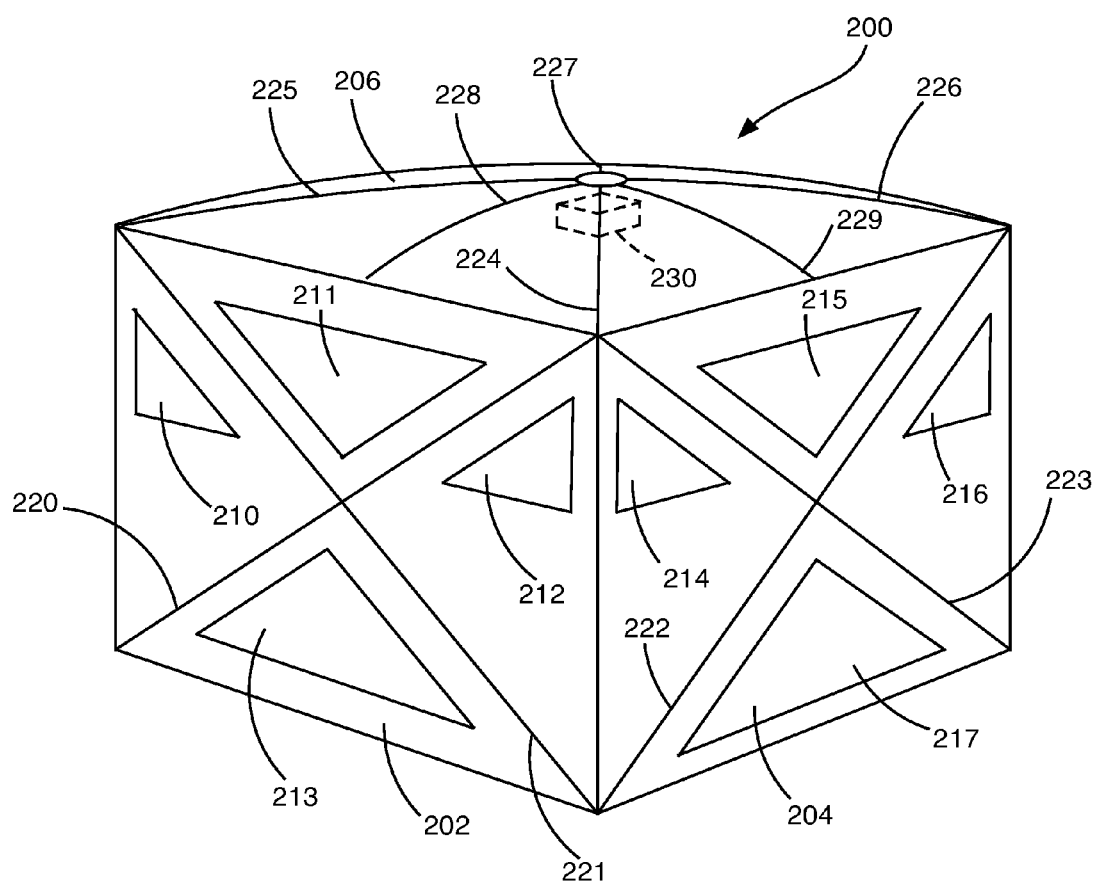
FIG. 10 is a perspective side view of a temporary structure with a descenting particle generator positioned therein in accordance with the principles of the present invention.

As illustrated in FIG. 10, a hunting blind, generally indicated at 200 in accordance with the principles of the present invention is illustrated. The hunting blind is generally a four-sided structure with sidewalls, such as sidewalls 202 and 204 and a roof 206. Each of the sidewalls, such as sidewalls 202 and 204, include a plurality of windows or vents, such as windows 210-212 for wall 202 and windows 214-216 for wall 204 and vent 213 for wall 202 and vent 217 for wall 204. Each of the windows and vents 210-217 is configured to be open and closeable from inside the blind 200 as by providing an inner flap that can be selectively zipped closed around the perimeter of the window or vent or unzipped to allow air to pass through the window or vent. Each window or vent 210-217 may also be provided with an outer screen that is left in place when the window or vent 210-217 is opened or closed. The blind 200 is supported by a plurality of support members 220-227, such as shock corded tent poles that are interconnected to form an internal or external frame for the blind 200. Additional support members 228 and 229 may be provided to support the weight of an ozone generator 230 that is suspended from the roof support members 224-229 proximate the roof 232 of the blind.

Figure 11:
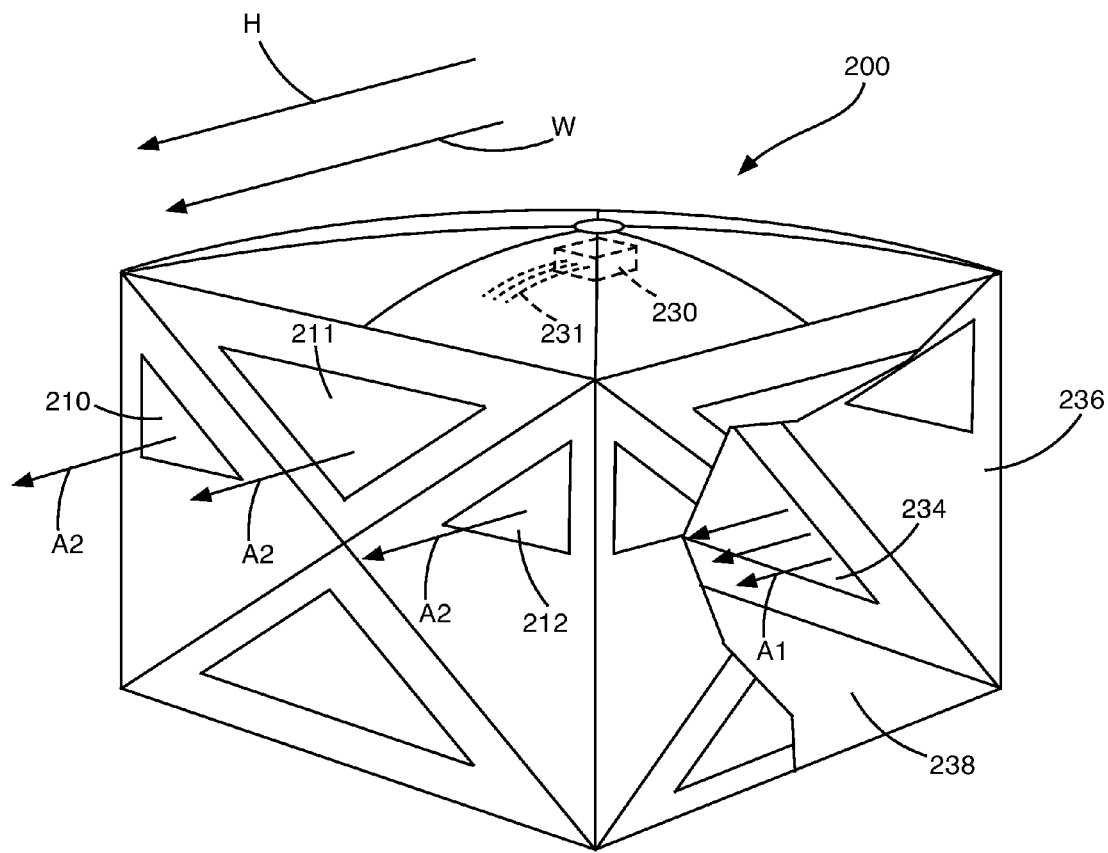
FIG. 11 is a perspective side view of a temporary structure with a descenting particle generator positioned therein in accordance with the principles of he present invention.

As further illustrated in FIG. 11, the blind 200 is positioned in an outdoor environment in which hunters may be positioned within the blind 200. In this example, as indicated by the direction of hunting arrow H, the blind 200 is actually positioned up wind from the wild game being hunted, as indicated by the direction of wind arrow W, a most undesirable condition when hunting animals that have a highly sensitive sense of smell and will flee the area if a human scent is detected. In order to control by masking and/or descenting air flowing from the blind 200, the ozone generator 230 is oriented within the blind 200 so as to emit ozone in the wind direction W. Because the windows 210, 211 and 212 will necessarily need to be open to allow the hunter to view the area being hunted, odors from within the blind 200 will emanate from the windows 210-212, and without being treated, will flow with the wind W toward the hunting area, potentially alerting animals to the presence of the blind 200 and the hunter or hunters. In order to improve interaction between the ozone 231 and the air A1 entering the blind 200, a lower vent 234 in the opposite side 236 of the blind 200 is opened to cause the air A to flow from a location near the floor 238 of the blind around the hunter (not shown) through the flow of ozone 231 and out the windows 210-212. This ensures that the ozone 231 and air A1 have adequate resonance time within the blind 200 to interact that will allow the ozone 231 to deodorize the air A2. By causing the air A1 to enter through a lower vent 234, silhouetting effects of the hunter within the blind 200 that would alert the game animal to the presence of the hunter within the blind 200 are eliminated, the air A1 must circulate through the blind 200 for a longer period of time than would be the case in a direct cross-flow situation and the ozone 231 being generated does not build within the blind 200 to potentially unsafe levels.

Figure 12:
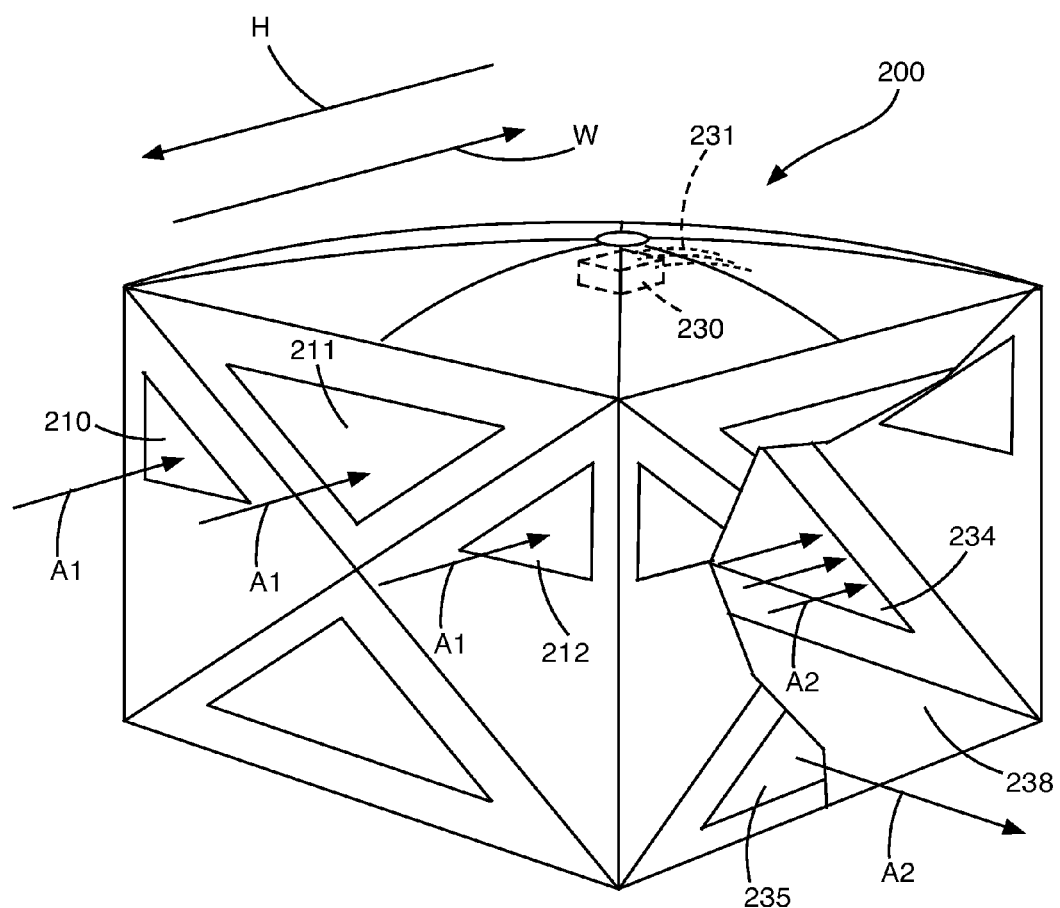
FIG. 12 is a perspective side view of a temporary structure with a descenting particle generator positioned therein in accordance with the principles of the present invention.

As shown in FIG. 12, when the wind direction W switches to a direction where the blind 200 is opposite to the direction of hunting H, the windows 210-212 will remain open to allow the hunter to view the desired hunting area. The ozone generator 230 will be reoriented to cause the ozone 231 to emanate from the ozone generator 230 in the direction of the wind W. The air A1 entering the blind 200 will then flow round the hunter (not shown) interact with the ozone 231 for a period of time. The ozonized air A2 will then exit the blind through the lower vents 234 and 235. Again, the vents 234 and 235 are positioned near the floor 238 of the blind 200 for reasons previously mentioned.

In order to provide evidence of the effectiveness of the blind/ozone generator configuration in eliminating odors as well as maintaining a desirable ozone concentration within a blind that is both safe and effective, tests were performed using a hunting blind having an interior volume of approximately 222 square feet with approximately six feet by six feet side walls and a 6 inch high pyramid shaped roof. An ozone generator was positioned within the blind. The ozone generator produced approximately 100 mg/hr ozone. A wind source was directed at the blind and produced a wind of between approximately 3 to 5 mph. An ozone analyzer was employed to measure ozone concentrations at various locations both inside and outside of the blind during testing. The various tests included measurement of ozone concentrations both inside and outside of the blind with various ozone generator positioning and wind directions relative to the blind. Surprisingly, by proper placement and orientation of the ozone generator within the blind, coupled with control of the airflow through the blind, ozone concentration within the blind in the hunter zone could be effectively minimized while maximizing ozone concentration of the ozone exiting the blind. Such a process provides for a safe environment for a hunter positioned within the blind while maximizing foreign scent/ozone interaction as the blown into the blind exits into the natural environment in a concentration that is known to be effective at eliminating detectable foreign scents by game animals. In other words, the tests prove that the ozone concentration within the blind in the hunter zone can be controlled to have a concentration that is lower than a concentration of ozone exiting the blind.

Prior to testing, ambient ozone levels were measured using the ozone analyzer. The ambient levels were measured at between approximately 0.02 to 0.03 ppm. Wind speed was measured with the anemometer at between approximately 3 to 5 mph. The test results are based on the ozone output of an ozone generator capable of producing approximately 100 mg/hr ozone. If an ozone generator is used that produces more or less ozone, adjustments to the position of the ozone generator within the blind and adjustments to window and vent openings can be made to accommodate any such ozone generator in accordance with the principles of the present invention. For example, if an ozone generator is operated at high power or boost mode, it may produce more than 100 mg/hr ozone. Thus, such a high power mode may be beneficial in higher wind conditions where an increase in ozone production is necessary to increase the ozone concentration in the blind without changing window, vent or ozone generator conditions. Likewise, if an ozone generator that only produces 50 mg/hr ozone is employed, the vent opening can be decreased by 50% to match the percent decrease in ozone production capability or the ozone generator can be moved further from the upper window opening to increase resonance time of the ozone produced within the blind before being vented from the blind by the controlled circulation of the present invention.

Figures 13A, 13B:
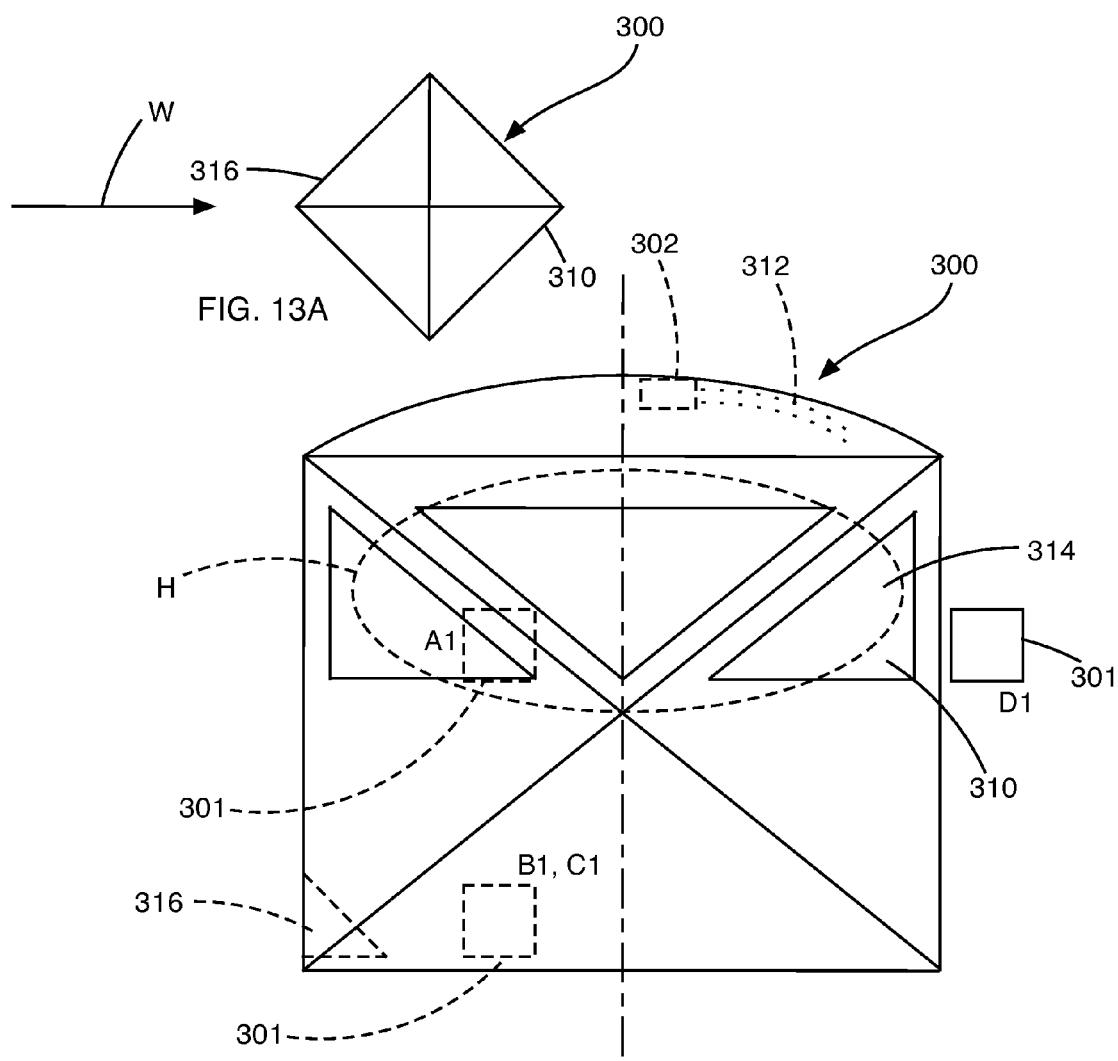
FIG. 13A is a top view of a temporary structure in relation to wind direction in accordance with the principles of the present invention.
FIG. 13B is a side view of the temporary structure shown in FIG. 13A.

In a first test setup where the wind was blowing in a direction as illustrated in FIG. 13A, which represents a top view of the blind 300. As shown in FIG. 13B, the ozone-producing outlet of the ozone generator 302 was faced toward the downwind windows, such as window 310, so that the ozone 312 being produced is directed in the same direction as the wind W. The open downwind windows defined an area of approximately 450 square inches. The open downwind windows were constructed with shoot through screens 314. Shoot through screens are typically formed of a polyester mesh fabric that permits airflow through the screen without impairing vision and are replaceable after holes have been made in the screens by passing bullets or arrows. Shoot through screens will have some effect on the flow of air through the blind 300 and thus affect the amount of ozone 312 that is retained within the blind 300, but is accounted for by the methods for controlling ozone concentration within the blind 300 according to the principles of the present invention. The mesh screens may have a camouflage pattern to match the camouflage pattern of the blind. Such shoot through screens allow a hunter to shoot through the screen while hunting without having to open the window, which movement and sound could startle a game animal.

The results of the first four test runs using the test setup described above are set forth in TABLE 1 below.

TABLE 1

| Test Run A1 | Test Run B1 | Test Run C1 | Test Run D1 |
|---|---|---|---|
| 1) 0.11 ppm | 1) 0.12 ppm | 1) 0.08 ppm | 1) 0.06 ppm |
| 2) 0.12 ppm | 2) 0.14 ppm | 2) 0.10 ppm | 2) 0.07 ppm |
| 3) 0.13 ppm | 3) 0.16 ppm | 3) 0.09 ppm | 3) 0.08 ppm |
| 4) 0.15 ppm | 4) 0.16 ppm | 4) 0.08 ppm | 4) 0.07 ppm |
| 5) 0.17 ppm | 5) 0.15 ppm | 5) 0.09 ppm | 5) 0.08 ppm |
| 6) 0.18 ppm | 6) 0.15 ppm | 6) 0.08 ppm | 6) 0.08 ppm |
| 7) 0.18 ppm | 7) 0.19 ppm | 7) 0.08 ppm | 7) 0.08 ppm |
| 8) 0.18 ppm | 8) 0.20 ppm | 8) 0.09 ppm | 8) 0.09 ppm |
| 9) 0.19 ppm | 9) 0.20 ppm | 9) 0.08 ppm | 9) 0.08 ppm |
| 10) 0.17 ppm | 10) 0.21 ppm | 10) 0.09 ppm | 10) 0.09 ppm |
| 0.16 Average ppm | 0.17 Average ppm | 0.09 Average ppm | 0.08 Average ppm |

In Test Run A1, an ozone analyzer 301 was positioned at a height of approximately 3 feet from ground level and approximately one foot back of center of the blind 300 where the head of a seated hunter would typically be positioned (i.e., in the hunter zone) within the blind 300. In Test Run B1, the ozone analyzer was positioned at a height of 6 inches from the floor and 1 foot back of center. In Test Run C1, the ozone analyzer was positioned in the same position as test A1 at a height of approximately 3 feet and about one foot back of center within the "hunter zone" as generally defined by ellipse H where the head of the hunter may be located within the blind 300 while hunting). However, in test C1, an upwind vent 316 window, defining an approximately 140 square inch area opening, near (e.g., approximately 6 inches above) the floor of the blind 300 was opened so that the wind W could flow into the vent 316, through the blind 300 and out the open windows, such as window 310. In test D1, the test was conducted with the ozone analyzer 301 was positioned at a height of approximately three feet and approximately 1 inch from an outer surface of the blind at the location of the open windows, such as window 310, to detect the ozone concentration as the air exited the blind. Samples were taken every minute for each test run, with total test duration lasting ten minutes for each test.

As illustrated through data collected in test runs A1 and B1, the ozone concentration within the blind started at near 0.1 ppm after the first minute of operation, but climbed to at or near 0.2 ppm after only 10 minutes of operation. Such a concentration is not considered safe for human exposure over an extended period of time if exposure is to exceed about 2 hours. This is due to the fact that air flow was restricted by not allowing fresh air to be blown into the blind through a vent opening to intermix with generated ozone that is then forced to exit through the open windows.

In tests C1 and D1, when the vent window was open, the ozone concentration within the blind was maintained inside the blind at between about 0.08 and 0.10 ppm, with a time weighted average of about 0.08 ppm. The air exiting the blind 300 had an ozone concentration of between about 0.06 and 0.09 ppm, with a time weighted average of 0.08 ppm.

The tests A1-D1 represent a worst-case scenario for a hunter in which the hunter is hunting up wind of a game animal. Moreover, a vent opening of only about 30% of the area of the window openings was effective of maintaining a safe ozone concentration within the blind 300 while providing an effective ozone air concentration outside the blind 300 for effectively eliminating foreign scents emanating from the blind 300.

In a second test setup, the wind was blowing in a direction as illustrated in FIG. 14A (i.e. upwind). As shown in FIG. 14B, the outlet of the ozone generator 302 was faced in different directions as set forth below. The windows, including window 310 defined an area of approximately 450 square inches. The windows were constructed with shoot through screens in place. Table 2 provides the test data for the second test setup.

TABLE 2

| Test Run A2 | Test Run B2 | Test Run C2 | Test Run D2 |
|---|---|---|---|
| 1) 0.09 ppm | 1) 0.05 ppm | 1) 0.05 ppm | 1) 0.12 ppm |
| 2) 0.12 ppm | 2) 0.06 ppm | 2) 0.04 ppm | 2) 0.12 ppm |
| 3) 0.11 ppm | 3) 0.07 ppm | 3) 0.03 ppm | 3) 0.12 ppm |
| 4) 0.11 ppm | 4) 0.09 ppm | 4) 0.04 ppm | 4) 0.11 ppm |
| 5) 0.11 ppm | 5) 0.08 ppm | 5) 0.03 ppm | 5) 0.12 ppm |
| 6) 0.10 ppm | 6) 0.07 ppm | 6) 0.04 ppm | 6) 0.11 ppm |
| 7) 0.10 ppm | 7) 0.08 ppm | 7) 0.03 ppm | 7) 0.12 ppm |
| 8) 0.10 ppm | 8) 0.07 ppm | 8) 0.04 ppm | 8) 0.13 ppm |
| 9) 0.10 ppm | 9) 0.07 ppm | 9) 0.03 ppm | 9) 0.09 ppm |
| 10) 0.10 ppm | 10) 0.08 ppm | 10) 0.04 ppm | 10) 0.12 ppm |
| 0.10 Average ppm | 0.07 Average ppm | 0.04 Average ppm | 0.12 Average ppm |

In test run A2, the ozone analyzer 301 was positioned at a height of approximately 3 feet and one foot back of center of the blind where a hunter would typically be positioned within the blind 300 (i.e., the hunter zone). The outlet of the ozone generator 302 was positioned so that ozone 312 was produced in a direction that faced the wind direction. Measurements were taken every minute for 10 minutes. The ozone concentration at the location of the analyzer 301 ranged from between about 0.09 and 0.12 ppm with a time weighted average of approximately 0.10 ppm.

In test run B2, the ozone analyzer 301 was positioned at a height of approximately 3 feet and one foot back of center of the blind where a hunter would typically be positioned within the blind 300 (i.e., the hunter zone). The ozone generator 302 was reversed so that the outlet of the ozone generator 302 was positioned away from the wind and toward the vent window 316. In Test Run C2, the ozone analyzer 301 was positioned at a height of approximately 3 feet and about one foot back of center with the upwind vent window 316 near (e.g., approximately 6 inches above) the floor of the blind 300 being open. The outlet of the ozone generator was positioned near the roof of the blind 300 at approximately 1.5 feet from the sidewall containing the vent window 316. In Test Run D2, the ozone analyzer 301 was positioned at a height of approximately six inches above the ground and approximately 1 inch from an outer surface of the vent window 316. The outlet of the ozone generator was positioned the same as in test A2. Ozone concentration measurements were taken every minute for a total of ten minutes for each test run.

In test run A2, the ozone concentration ranged from between about 0.09 and 0.12 ppm with a 0.10 ppm time weighted average. In test run B2, the ozone concentration ranged from between about 0.05 and 0.09 ppm with a 0.07 ppm average. Test run C2 produced ozone concentrations of between about 0.03 and 0.05 ppm with an approximate a time weighted average of 0.04 ppm. In test run D2, the ozone concentration ranged from about 0.09 and 0.13. By orienting the ozone generator 302 so that ozone is discharged in a downwind direction, as in test runs B2 and C2, the ozone concentration within the blind can be minimized while still maintaining an effective ozone concentration in air exiting the blind as shown in test run D2. In fact, the concentration of ozone exiting the blind is actually higher than the ozone concentration in the hunter zone, which provides an ideal situation for providing a safe and effective way to use ozone in a partially enclosed structure to descent foreign scents that are exiting the structure. This discovered phenomenon is particularly surprising and beneficial. That is, one would not expect the ozone concentration exiting the blind to be greater than the ozone concentration within the blind. At a minimum, one might expect the ozone concentration of air exiting the blind to be the same as that within the blind. However, knowing that by directing an air flow through the blind in an indirect path from an upper window to a lower vent, there is a way by which the hunter can achieve maximum ozone concentration in the air that exits the blind to continue to descent the air as it reenters the surrounding environment while minimizing the hunters exposure to ozone within the blind.

Thus, as wind conditions change, the test results show that moving the ozone generator closer to or further away from the side of the blind 300 where the vent window is located affects the ozone concentration in the hunter zone. That is, by moving the ozone generator further from the side of the blind containing the vent window, the ozone concentration within the blind 300 will increase. This will be beneficial in higher wind conditions since a greater volume of air will pass through the blind as the wind speed increases. Thus, the hunter may want to move the ozone generator further from the vent window side of the blind 300 when the wind speed is greater than about 5 mph. Conversely, when the wind speed decreases below about 3 mph, the hunter may want to move the ozone generator closer to the vent window &de of the blind to decrease the ozone concentration in the hunter zone while maintaining an effective ozone concentration in the air exiting the blind. Thus, the hunter should monitor the surrounding wind speed to properly position the ozone generator within the blind according to the principles of the present invention.

Test runs A2 and B2 depict minimally ventilated hunting situations where, with improper ventilation within the blind higher levels of ozone will reside within the hunter zone of the blind 300. However, by changing the position and/or orientation of the ozone generator along with opening one or more properly placed vent windows in the lower portion of the blind 300, the ozone levels in the hunter zone can be lowered to a safe level while still providing effective scent control. For example, as shown in Test C1, by opening a vent of less than half the size of the open hunting windows, the ozone concentration decreased by about half to a level that is considered to be safe for extended human exposure. In tests A2 and B2, where the wind was in the opposite direction, by changing the outlet direction of the ozone generator to be with the wind, the ozone concentration was decreased by about one third to a half. Also surprisingly, by positioning the ozone generator nearer to the vent side of the blind to be about half the distance from the center of the blind to the wall containing the vent window, the ozone concentration within the blind 300 in the hunter zone was decreased to near measured ambient conditions (i.e., within about 0.01 ppm), while still providing a sufficiently high ozone concentration outside the blind 300 in the air exiting the blind through the vent window to control foreign scents. As such, it has been shown that an ozone generator can be safely operated within an at least partially enclosed structure, such as a hunting blind, while maintaining an effective ozone concentration in air exiting the blind that contains foreign scents to mask or otherwise remove these scents from the exiting air to become virtually undetectable by game animals and the like.

Again, it is important to note that use of vent windows that are positioned below the level of the shooting windows of the blind minimizes backlighting of the hunter or hunters positioned within the blind. Otherwise, in a configuration where a window on the opposite side of the blind is open to allow cross-flow of air through the blind a silhouette of the hunter(s) would be visible outside the blind potentially alerting a game animal to the presence of the hunter within the blind. The present invention provides a hunting blind that allows cross-flow of air through the blind without silhouetting of the hunter(s). The indirect path of the cross-flow of air through the blind also helps to decrease ozone concentrations in the hunter zone while maximizing ozone concentration of air exiting the blind.

Thus, the experimental tests provide confirmation of the construction of a hunting blind according to the present invention with the following results being demonstrated by the tests. In the test runs A1 and B1, a minimally ventilated hunting blind was provided that resulted in a significant concentration level of ozone in the hunter zone of the blind, with averages of 0.16 to 0.17 ppm. By opening additional lower venting, the level can be reduced to a safe, yet effective, level by opening additional floor vents and/or the position of the ozone generator. In test C1, a ground level vent of about one third of the size of the hunting windows was opened. As a result, the ozone level recorded decreased by approximately one third of the previous ppm average.

In the second set of tests, test A2 and B2 where the wind is opposite to that of test C1, manipulating the outlet direction of the ozone generator caused a significant reduction of the ozone concentration. In Test C2, the ozone generator was positioned closer to the vent by approximately half the distance, which resulted in a near ambient level of ozone in the hunter zone. Test D2 proves that an increase in the ozone concentration as it exits vent opening can be achieved according to the principles of the present invention.

In order to confirm these results, additional tests were conducted using the blind setup of FIG. 14B. The test results are set forth in Table 3.

TABLE 3

| Test Run "E2" | | Test Run "F2" | | Test Run "G2" | |
|---|---|---|---|---|---|
| Inside | Outside | Inside | Outside | Inside | Outside |
| 1  0.04 ppm | 0.20 ppm | 1  0.09 ppm | 0.10 ppm | 1  0.10 ppm | 0.14 ppm |
| 2  0.05 ppm | 0.21 ppm | 2  0.11 ppm | 0.14 ppm | 2  0.12 ppm | 0.14 ppm |
| 3  0.05 ppm | 0.20 ppm | 3  0.10 ppm | 0.14 ppm | 3  0.11 ppm | 0.15 ppm |
| 4  0.05 ppm | 0.20 ppm | 4  0.09 ppm | 0.17 ppm | 4  0.10 ppm | 0.15 ppm |
| 5  0.04 ppm | 0.20 ppm | 5  0.09 ppm | 0.15 ppm | 5  0.11 ppm | 0.14 ppm |
| 6  0.05 ppm | 0.19 ppm | 6  0.10 ppm | 0.14 ppm | 6  0.12 ppm | 0.16 ppm |
| 7  0.05 ppm | 0.22 ppm | 7  0.10 ppm | 0.16 ppm | 7  0.13 ppm | 0.18 ppm |
| 8  0.05 ppm | 0.16 ppm | 8  0.10 ppm | 0.14 ppm | 8  0.12 ppm | 0.17 ppm |
| 9  0.05 ppm | 0.19 ppm | 9  0.09 ppm | 0.12 ppm | 9  0.11 ppm | 0.21 ppm |
| 10  0.05 ppm | 0.20 ppm | 10  0.10 ppm | 0.19 ppm | 10  0.12 ppm | 0.15 ppm |
| 0.05 Avg. ppm | 0.20 Avg. ppm | 0.10 Avg. ppm | 0.15 Avg. ppm | 0.11 Avg. ppm | 0.16 Avg. ppm |

In test run E2, the ozone generator was positioned about one foot from the downwind wall of the blind and near the roof with the ozone outlet facing the downwind windows (position C2). In this configuration, two tests were conducted, one with the ozone analyzer in the hunter zone (position A2, B2, C2) and the second with the ozone analyzer positioned just outside the downwind windows (position D2).

In test run F2, the ozone generator was positioned about two feet from the downwind windows (between positions B2 and C2). As a result, the ozone concentration within the blind increased and the ozone concentration of the air exiting the blind at the hunting windows slightly decreased. In both E2 and F2, however, the ozone concentration in the hunting zone is significantly lower than the ozone concentration in the air exiting the blind. Finally, in test G2, the ozone generator was positioned near the center of the blind with the ozone outlet facing the downwind open window (position B2). There was a slight increase in the ozone concentration within the blind and no statistical difference in the ozone concentration of the air exiting the blind.

Accordingly, the tests conducted according to the principles of the present invention prove that the ozone concentration within a blind or other temporary structure can be controlled and maintained at effective and acceptable levels for human exposure. Specifically, with a prescribed combination of window and vent openings and ozone generator position and orientation, the ozone concentration within the hunter zone of the blind can be maintained at a time weighted average of between about 0.04 and 0.1 ppm with a more ideal time weighted average concentration of between about 0.05 and 0.09 ppm regardless of wind direction. Ideally, the concentration of ozone within the hunting zone may be maintained at about a time weighted average of about 0.08 ppm. Moreover, the time weighted average concentration of ozone emanating from the blind can be maintained at between about 0.7 ppm and 0.2 ppm with a more ideal time weighted average concentration of between about 0.1 ppm and 0.2 ppm so that the ozone within the air emanating from the blind will continue to comingle with the ozone particles to continue to descent and/or masque foreign scents within the air as such are intermixes with ambient air outside of the blind. Such a concentration differential between that which is present within the hunter zone and that which is emanating from the blind provides the best possible scenario in which a maximum concentration of ozone is present in air leaving the blind to eliminate detectable odors outside the blind while limiting ozone exposure within the hunting zone to acceptable levels.

Figure 15A:
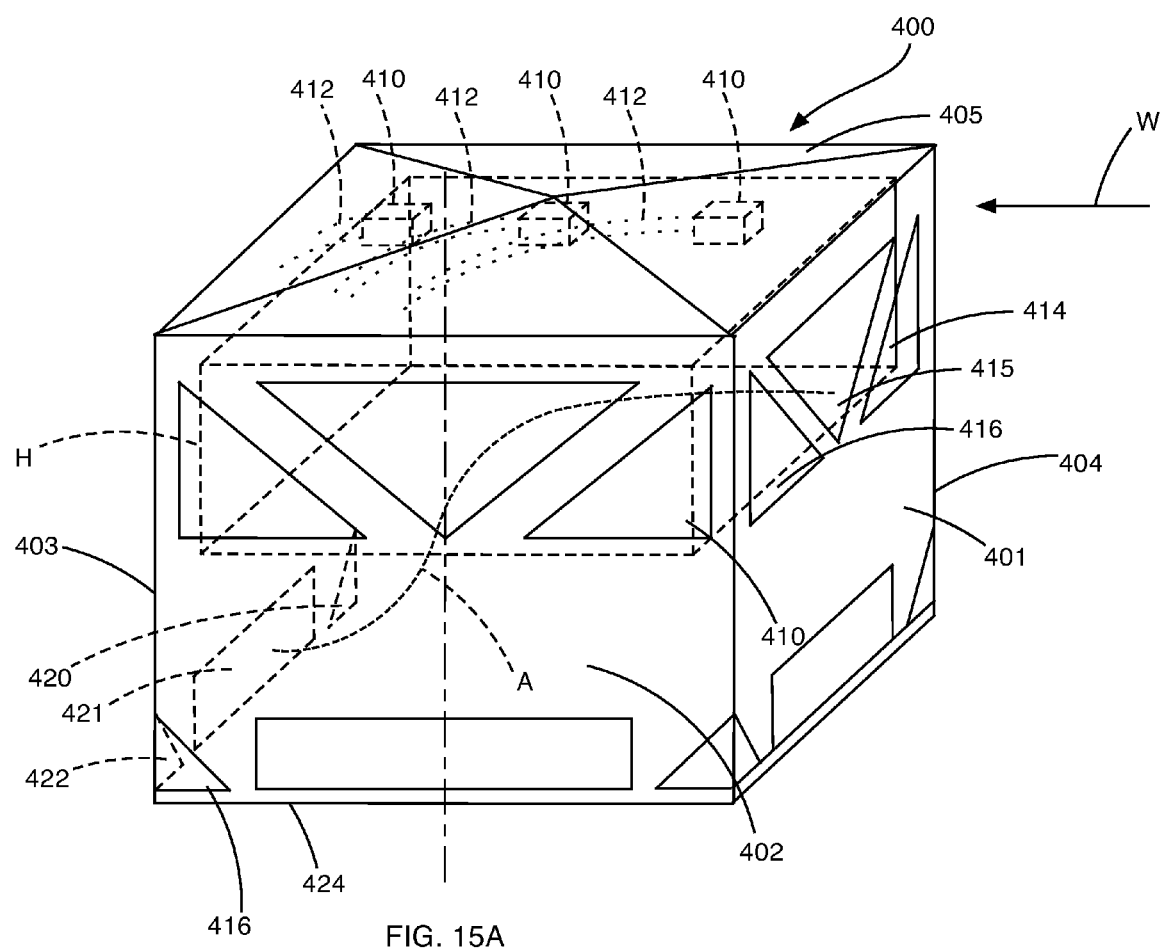
FIG. 15A is a perspective side view of a temporary structure in relation to a first wind direction in accordance with the principles of the present invention.
Figure 15B:
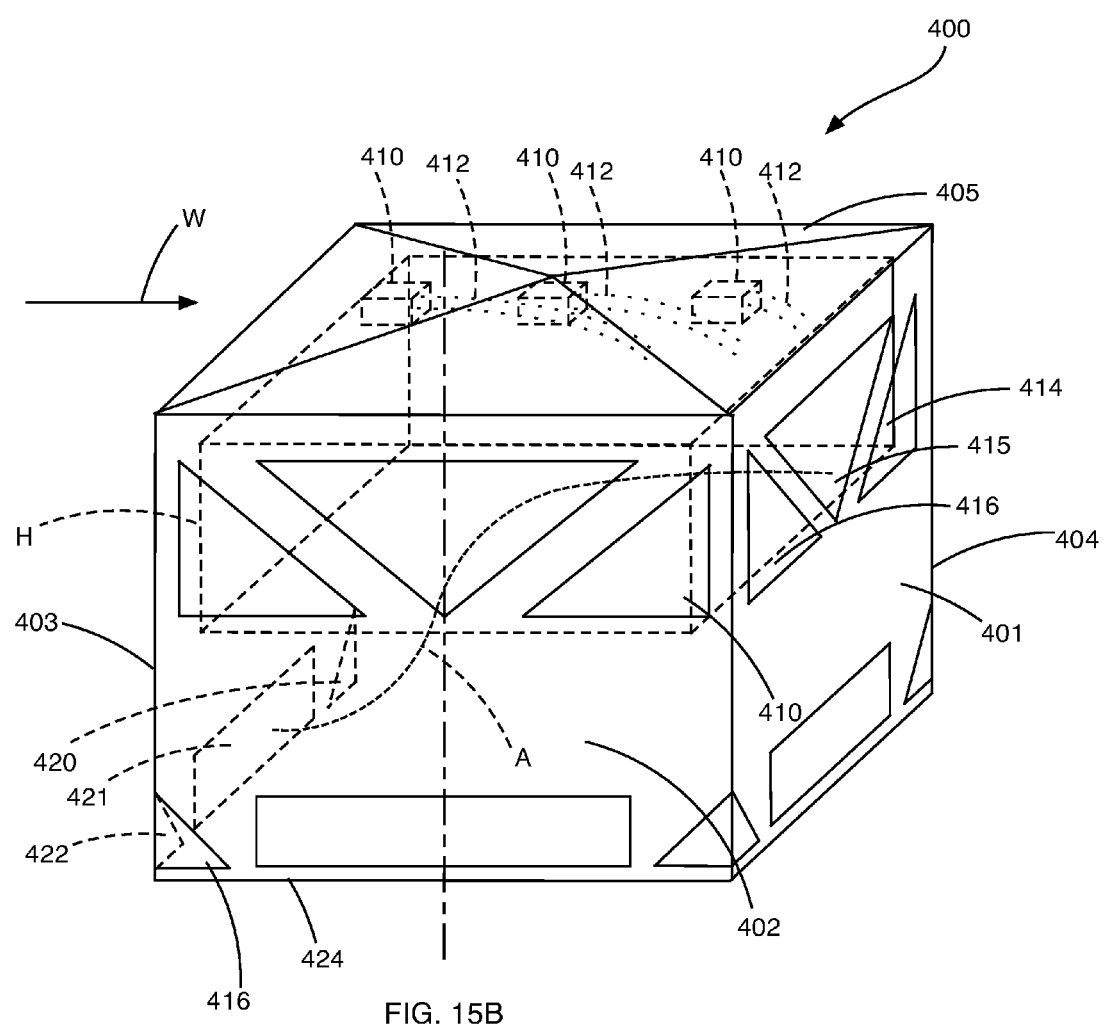
FIG. 15B is a side view of the temporary structure shown in FIG. 15A in relation to a second wind direction.

As illustrated in FIGS. 15A and 15B, a temporary structure in the form of a hunting blind 400 having four side walls 401-404 and a roof 405 is illustrated. Positioned within the blind 400 is a descending particle generator in the form of an ozone generator 410 that emits descending particles in the form of ozone (O3) particles. In FIG. 15A, the wind W is blowing in a desired downwind direction in which the blind 400 has been positioned downwind of the game animal being hunted and the wind is blowing toward the primary viewing side 401 of the blind 400. In order to provide a desired circulation path of air flowing through the blind 400 while allowing a hunter positioned within the blind 400 to view the surroundings through the windows 414-416, windows 414-416 will be open (although they may be covered with shoot through screens in place to conceal the lower extremities of the hunter and any equipment that may be placed on the ground). In addition, one or more lower vent windows 420-422 have been opened. The lower vent windows are positioned at or near the floor or bottom edge 424 of the blind 400. It is also contemplated that the lower vent windows 420-422 could be positioned at a level that is below the upper viewing windows 414-416 so as to prevent silhouetting as previously discussed. The ozone generator 410 is positioned proximate the roof 405 within the blind 400 and oriented with its output facing away from the wind W. As such, the particles 412 being emitted will be drawn by the wind W once it enters the blind 400 toward the back of the blind 400, that is, toward the open vent side 403 of the blind 400. Because ozone particles 412 are heavier than air, they will naturally flow in a downward path toward the floor 424 of the blind where the vent windows 420-422 are located. As the air A passes through the blind 400 it will flow through the hunter zone H, pick up any foreign scents and intermix with the ozone particles 412 that will effectively descent the air A both during its resonance time within the blind and subsequently as it exits the blind 400 through the open vent windows 420-422. As illustrated by the foregoing test data, this configuration prevents any buildup within the blind 400 of ozone particles 412 and minimizes ozone exposure within the hunter zone H while maximizing ozone concentration as the ozone/air mixture exits the blind 400 through the vent openings 420-422. Accordingly, fresh air entering the blind 400 through the viewing windows 414-416 first passes through the hunting zone H to provide a flow of fresh air to the head of the hunter.

Depending on wind speed, the ozone generator 410 can be positioned at various locations within the blind 400 that are generally centered relative to the open windows 414-416. In low wind conditions (e.g., below about 3 miles per hour), the ozone generator 410 may be positioned near the back wall 403 of the blind 400. Doing so will decrease the resonance tune of the ozone within the blind 400 since the ozone particles 412 will be more quickly vented from the blind 400 and also directs the flow of ozone particles 412 away from the hunter zone H. In a high wind environment (e.g., above about 10 miles per hour), the ozone generator may be positioned closer to the front wall 401 of the blind 400. Doing so will increase the resonance time of ozone 412 in the blind as it passes over and through the back portion of the hunter zone H to maintain a safe but adequate ozone concentration within the blind 400 while minimizing ozone exposure to the hunter.

If the wind W is blowing in the opposite direction in which the hunter is effectively hunting up wind (i.e., the most undesirable location for a hunter) as shown in FIG. 15B, the same S-shaped airflow path A is created within the blind. The differences are that the air flow is directed through the open vent windows 420-422 generally along the S-shaped path and out viewing windows 414-416 and the ozone generator 410 is reversed so that the ozone particles 412 are emitted in a downwind direction toward the open viewing windows 414-416. Again, the position of the ozone generator 410 within the blind 400 can be adjusted based on the wind speed, with the ozone generator 410 being positioned further back in the blind in higher wind conditions and more forward in lower wind conditions to maintain a relatively consistent ozone concentration within the blind 400 in all wind conditions.

In both illustrated examples of FIGS. 15A and 15B, airflow A through the blind 400 is directed along an S-shaped path between one or more upper windows and one or more lower vents with the direction of the air flow depending on the wind and hunting directions. The ozone generator is positioned above or at the top of the hunting zone and pointed in a direction so that ozone particles are being emitted in the same direction as the wind. This provides for more efficient operation of the ozone generator, so that the fan of the ozone generator is not working against the flow of air within the blind and, importantly, to provide a cascade of ozone particles around the hunter zone so as to minimize ozone exposure by the hunter while maximizing ozone concentration as air A exits the blind 400. Doing so provides a higher concentration of ozone where, under normal conditions, the head of the hunter is not located to minimize the ozone concentration in the hunter zone while maintaining sufficient ozone concentrations outside the hunter zone for descanting air within the blind and continuing to descent the air as it emanates from the blind and reenters the surrounding environment.

Thus, according to the present invention, foreign scents can be eliminated from air leaving a temporary structure, such as a hunting blind, by applying a low volume stream of an oxidizing gas comprising ozone or hydroxyl and hydroperoxide ions within the blind and forcing the air within the blind to flow along a prescribed path depending on wind direction. The gaseous stream may be applied by an ozone generator in an enclosed or partially enclosed space in a quantity that is safe for humans. While the present invention has been primarily described with reference to hunting applications, the present invention could also be use to control human scents of a military person desiring to escape detection by other humans or scent animals (e.g. dogs) sufficiently to avoid detection and evade capture.

It is also contemplated that the temporary structure of the present invention could be treated with ozone before or after being installed in the field to eliminate odor emanating from the exterior surfaces of the temporary structure itself.

Small ozone generators, such as those producing 1 to 25 lbs. of ozone per day, can be utilized. Also the ozone can be applied from compressed ozone-filled containers similar to compressed air. Portable low volume ozone generators, which generate up to 65 mg/hr of ozone, are sold by EcoQuest International of Greeneville, Tenn. EcoQuest also sells generators that produce hydroxyl and hydroperoxide ions. Thus, it will be appreciated by persons skilled in the art that numerous sizes, production capacities and types of ion particle generators may be made to the invention without departing from the spirit or scope of the invention as broadly claimed.

Thus, the present invention discloses methods of reducing or of eliminating any scent that is foreign to the environment from the clothing, equipment and body of a hunter, by generating a volume of descenting particles, such as by an ozone gas or a gaseous stream of hydroxyl and hydroperoxide ions produced by catalytic ionization within an enclosed or partially enclosed space, such as a hunting blind, within which the hunter or hunters are present. It is understood that the terms “hunter” and “sportsman” are meant to include those individuals who may hunt with a camera or who merely enter an environment to observe animals in their habitat. The particles or gas is applied to air entering the temporary structure to descent the clothing, equipment and body of the sportsman within the temporary structure while the sportsman is in the field. It is also contemplated that the devices and methods of the present invention may include delivering a gas in compressed/generated form from a generator that is a container.

It is to be understood for any embodiment disclosed herein that mentions an “ozone generator” that a descenting material generator may be used that produces ozone and/or any, each of, and/or all descenting materials referred to herein and their equivalents, with or without an integrated fan that is operating. In the systems set forth in the figures, any suitable ozonator, ozone generator, or descenting material generator may be used, with or without a fan that is operating.

The present invention therefore provides a method for reducing foreign scent in an enclosed or partially enclosed space, the method including: generating descenting particles with a generator, introducing the descenting particles into an enclosed or partially enclosed space in which one or more hunters or other sportsmen are present, the space containing foreign scent, and reducing the foreign scent in the space and air emanating from the space with the descenting particles. Such a method may include one or some, in any possible combination, of the following: the foreign scent including human odor; exposing the human being to about 0.1 or less ppm ozone over an extended period of time to continually reduce foreign scent, e,g, over a time period of eight hours or less. It is noted that all “ppm” ozone levels are a time-weighted average value in air.

The present invention, therefore, provides a system for reducing foreign scent in an open space between a temporary structure and an animal, the system including a generator for producing descenting particles housed within a temporary structure, such as a hunting blind.

The illustrated embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated. Those skilled in the art who have the benefit of this invention, its teachings, and suggestions will appreciate that the conceptions of this disclosure may be used as a creative basis for designing other structures, methods and systems for carrying out and practicing the present invention.

While there have been described various embodiments of the present invention, those skilled in the art will recognize that other and further changes and modifications may be made thereto without department from the spirit of the invention, and it is intended to claim all such changes and modifications that fall within the true scope of the invention. It is also understood that, as used herein and in the appended claims, the singular forms "a," "an," and "the" include plural reference, unless the context clearly dictates otherwise.

Unless defined otherwise, all technical and scientific terms used herein have the same meanings as commonly understood by one of ordinary skill in the art to which this invention belongs. While various methods and structures of the present invention are described herein, any methods or structures similar or equivalent to those described herein may be used in the practice or testing of the present invention. All references cited herein are incorporated by reference in their entirety and for all purposes. In addition, while the foregoing advantages of the present invention are manifested in the illustrated embodiments of the invention, a variety of changes can be made to the configuration, design and construction of the invention to achieve those advantages including combinations of components of the various embodiments. Hence, reference herein to specific details of the structure and function of the present invention is by way of example only and not by way of limitation.

What is claimed is:

1. A method of controlling a concentration of ozone within a temporary structure, comprising:

providing a substantially enclosed temporary structure comprising:

a plurality of sidewalls and a roof interconnected with the sidewalls;

a plurality of selectively openable and closeable upper windows, each sidewall having at least one upper window disposed therein;

a plurality of selectively openable and closeable lower vents, each side wall having at least one lower vent disposed therein, the lower vents being disposed at a location between a lower edge of a respective side wall and a lower edge of a respective upper window;

providing a descenting particle generator, the descenting particle generator being disposed within and coupled to the temporary structure proximate a roof thereof and oriented so that an outlet of the descenting particle generator is facing downwind;

opening at least one of the plurality of upper windows in the sidewall facing a hunting direction:

opening at least one of the plurality of vents in the sidewall opposite the at least one of the plurality of upper windows that is open; and activating the descenting particle generator to produce descenting particles within the temporary structure to intermix with odors present within the temporary structure and to descent the odors as the odors emanate from the temporary structure so as to be substantially non-detectable by animals present outside of the temporary structure, the at least one of the plurality of upper windows and plurality of vents being open a sufficient amount to cause air to be blown by wind through the temporary structure between the at least one open window and the at least one open vent.

2. The method of claim 1, wherein the descenting particles comprise ozone and further comprising maintaining a time weighted average concentration of ozone of between about 0.04 and 0.1 ppm within a hunting zone of the temporary structure.

3. The method of claim 1, wherein the descenting particles comprise ozone and further comprising maintaining a time weighted average concentration of ozone of between about 0.05 and 0.09 ppm within a hunting zone of the temporary structure.

4. The method of claim 1, wherein the descenting particles comprise ozone and further comprising maintaining a time weighted average concentration of ozone of about 0.08 ppm within a hunting zone of the temporary structure.

5. The method of claim 2, further comprising maintaining a time weighted average concentration of ozone exiting the temporary structure of a time weighted average of between about 0.07 and 0.2 ppm.

6. The method of claim 5, further comprising maintaining a time weighted average concentration of ozone within the hunting zone that is less than a time weighted average concentration of ozone exiting the temporary structure.

7. The method of claim 1, further comprising providing the plurality of lower vents proximate a lower edge of a respective side wall to prevent silhouetting through the temporary structure.

8. The method of claim 1, further comprising providing the temporary structure in the form of a hunting blind.

9. The method of claim 1, further comprising providing each of the plurality of vents in each side wall with a total opening area that is less than an opening area of the at least one window in the opposite sidewall.

10. The method of claim 8, further comprising providing each of the plurality of vents in each side wall with a total opening area that is about one third of a total opening area of the at least one window in the opposite sidewall.

11. The method of claim 2, further comprising positioning the descenting particle generator above a hunter zone within the temporary structure and directing ozone away from the hunter zone to minimize ozone concentration within the hunter zone.

12. The method of claim 2, further comprising sizing the ozone generator and temporary structure to maintain a time weighted average ozone concentration within the temporary structure of between about 0.04 and 0.1 ppm.

13. The method of claim 1, further comprising closing the plurality of vents in the side walls except for the at least one of the plurality of vents.

14. The method of claim 8, further comprising closing the plurality of upper windows in the side walls except for the at least one of the plurality of upper windows.

15. The method of claim 2, further comprising opening at least one additional vent to lower an ozone concentration within the temporary structure to between about 0.04 ppm and 0.1 ppm if a wind speed drops below about 3 mph.

16. The method of claim 2, further comprising moving the descenting particle generator in a downwind direction within the blind to lower the ozone concentration within the hunting zone.

17. The method of claim 2, further comprising at least partially closing at least one vent to increase the ozone concentration within the hunter zone of the temporary structure to between about 0.04 ppm and 0.1 ppm if a wind speed increases above about 5 mph.

18. The method of claim 2, further comprising moving the descenting particle generator in an upwind direction within the blind to raise the ozone concentration within the hunting zone.

* * * * *